United States Patent [19]

Misra

[11] Patent Number: 4,910,208
[45] Date of Patent: Mar. 20, 1990

[54] METHOD OF INHIBITING LEUKOTRIENE BIOSYNTHESIS BY ORAL ADMINISTRATION OF P-AMINOPHENOLS OR DERIVATIVES THEREOF

[75] Inventor: Raj N. Misra, Hopewell, N.J.

[73] Assignee: E. R. Squibb & Sons, Inc., Princeton, N.J.

[21] Appl. No.: 157,759

[22] Filed: Feb. 19, 1988

Related U.S. Application Data

[63] Continuation-in-part of Ser. No. 791,964, Oct. 28, 1985, abandoned.

[51] Int. Cl.$^4$ .................. A61K 31/24; A61K 31/47
[52] U.S. Cl. ...................... 514/311; 514/312; 514/534; 514/546; 514/654; 514/655; 514/657; 514/826; 514/863
[58] Field of Search ............... 514/311, 312, 654, 655, 514/657, 534, 546

[56] References Cited

U.S. PATENT DOCUMENTS

| | | | |
|---|---|---|---|
| 3,819,637 | 6/1974 | Bell | 260/288 R |
| 3,948,990 | 4/1976 | Barlow et al. | 564/429 X |
| 4,423,065 | 12/1983 | Clinton et al. | 514/657 X |
| 4,492,704 | 11/1985 | Fleisch et al. | 514/826 X |
| 4,496,590 | 1/1988 | Schlegel et al. | 514/826 X |
| 4,510,139 | 4/1985 | Bailey | 514/234 |
| 4,515,980 | 5/1985 | Bailey | 560/45 |
| 4,526,999 | 7/1985 | Durett et al. | 514/826 X |

FOREIGN PATENT DOCUMENTS

| | | | |
|---|---|---|---|
| 79141 | 10/1981 | European Pat. Off. | |
| 81321 | 6/1983 | European Pat. Off. | |
| 122518 | 10/1984 | European Pat. Off. | |
| 530825 | 8/1931 | Fed. Rep. of Germany | 564/429 |

OTHER PUBLICATIONS

Jambuservala, Holt, Mason, Soc. 1931 373, 375.
I. G. Farbenind, D.R.P. 580519 (1932); Frdl. 20,490.
Kehrmann, Neil, B. 47, 3102-Krystalle (aus Benzol).
Hey, Lawton, Soc. 1940 384, 387.
I. G. Farbenind, Scheiz. P. 135643 (1927).
I. G. Farbenind, D.R.P. 642,549.
Borsche, Hahn, B. 82 (1949) 260, 262.
I. G. Farbenind, D.R.P. 530,825 (1926); Frdl. 18 604.
Burcherer, Stohmann, C. 1904 I, 1012, -Blattchen.
"Antiinflammatory 2-(Aminomethyl)Phenols. Structure-Activity RElationship", Itoh et al.
"Biochemical and Pharmacological Activities of Ono-3122, A Diruetic, and Ono-3144, A Novel Anti--Inflammatory Drug," Aishita et al.

Primary Examiner—Leonard Schenkman
Attorney, Agent, or Firm—Burton Rodney

[57] ABSTRACT

A method is provided for inhibiting leukotriene biosynthesis and thus treating asthma, psoriasis or inflammation by oral administration of p-aminophenols having the structure

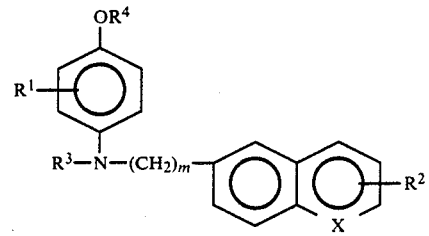

wherein m is 0 to 5; X is CH or N; $R^1$ and $R^2$ may be the same or different and are H, lower alkyl, aryl, hydroxy, hydroxyalkyleneoxy, alkylthio, alkoxy, alkanoyloxy, aryloxy, halo, carboxy, alkoxycarbonyl or amido; $R^3$ is H, lower alkyl, alkanoyl or aroyl; and $R^4$ is H, lower alkyl, benzoyl or alkanoyl, and including acid-addition salts thereof, with the proviso that when $R^4$ is benzoyl, $R^2$ is other than H.

22 Claims, No Drawings

METHOD OF INHIBITING LEUKOTRIENE BIOSYNTHESIS BY ORAL ADMINISTRATION OF P-AMINOPHENOLS OR DERIVATIVES THEREOF

REFERENCE TO OTHER APPLICATIONS

This application is a continuation-in-part of application Ser. No. 791,964, filed Oct. 28, 1985 now abandoned.

DESCRIPTION OF THE INVENTION

The present invention relates to a method of inhibiting leukotriene biosynthesis to treat inflammation or psoriasis or for treating asthma by orally administering p-aminophenols and derivatives thereof. These compounds have the structural formula

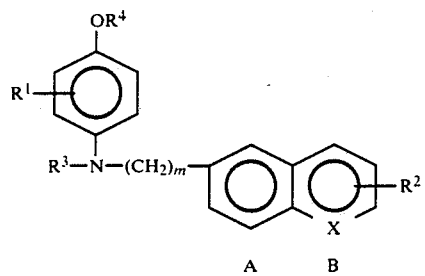

wherein m is 0 to 5; X is CH or N; $R^1$ and $R^2$ may be the same or different and may be H, lower alkyl, aryl, hydroxy, hydroyalkyleneoxy, alkylthio, alkoxy, alkanoyloxy, aroyloxy, halo, carboxy, alkoxycarbonyl or amido; $R^2$ may be a substituent on either or both the A ring or B ring (with the B ring being preferred; $R^3$ is H, lower alkyl, alkanoyl or aroyl; and $R^4$ i H, lower alkyl, benzoyl or alkanoyl, and including pharmaceutically acceptable salts thereof, with the proviso that when $R^4$ is benzoyl, $R^2$ is other than H or when $R^4$ is H, $R^3$ is H, X is CH and m is O, $R^1$ is other than H.

As to the pharmaceutically acceptable salts, those coming within the purview of this invention include the pharmaceutically acceptable acid-addition salts. Acids useful for preparing these acid-addition salts include, inter alia, inorganic acids, such as the hydrohalic acids, (e.g., hydrochloric and hydrobromic acid), sulfuric acid, nitric acid and phosphoric acid, and organic acids such as maleic, fumaric, tartaric, citric, acetic, benzoic, 2-acetoxybenzoic, salicylic; succinic acid, theophylline, 8-chlorotheophylline, p-aminobenzoic, p-acetamidobenzoic or methanesulfonic.

In addition, a method is provided for treating asthma mediated by leukotrienes in a mammalian species in need of such treatment, which method includes the step of orally administering to a mammalian host an effective amount of a compound of formula I or a pharmaceutically acceptable salt thereof or an N-naphthyl-p-aminophenol of the structure

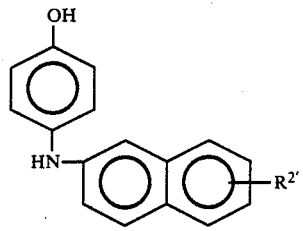

wherein $R^{2'}$ is H, OH or alkoxy or an aminophenol of the structure

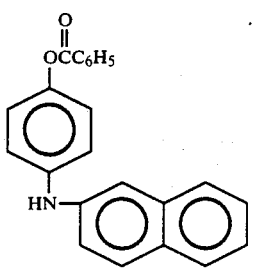

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups and/or 1 or 2 hydroxy groups.

The term "aralkyl", "aryl-alkyl" or "aryl-lower alkyl" as used herein refers to lower alkyl groups as discussed above having an aryl substituent, such as benzyl.

The term "halogen" or "halo" as used herein refers to chlorine, bromine, fluorine or iodine with chlorine being preferred.

The term "alkylthio" includes any of the above lower alkyl groups linked to a sulfur atom.

The term "hydroxyalkyleneoxy" refers to a group of the structure $HO-(CH_2)_n-O-$ wherein n is 2 to 8 and $(CH_2)_n$ is as defined below.

The terms "alkanoyl" and "aroyl" refer to a lower alkyl group linked to a carbonyl group and an aryl group linked to a carbonyl group, respectively.

The terms "lower alkoxy", "alkoxy", "aralkoxy", "alkanoyloxy", and "aroyloxy" include any of the above lower alkyl, aralkyl, alkanoyl and aroyl groups linked to an oxygen atom.

The term "alkoxycarbonyl" refers to a group of the structure

The term "amido" refers to

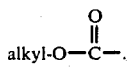

The terms $(CH_2)_m$ and $(CH_2)_n$ include straight or branched chain radicals having from 0 to 5 carbons in the normal chain in the case of $(CH_2)_m$, from 1 to 8 carbons in the normal chain in the case of $(CH_2)_n$ and may contain one or more lower alkyl and/or halogen substituents. Examples of $(CH_2)_m$ and $(CH_2)_n$ groups include

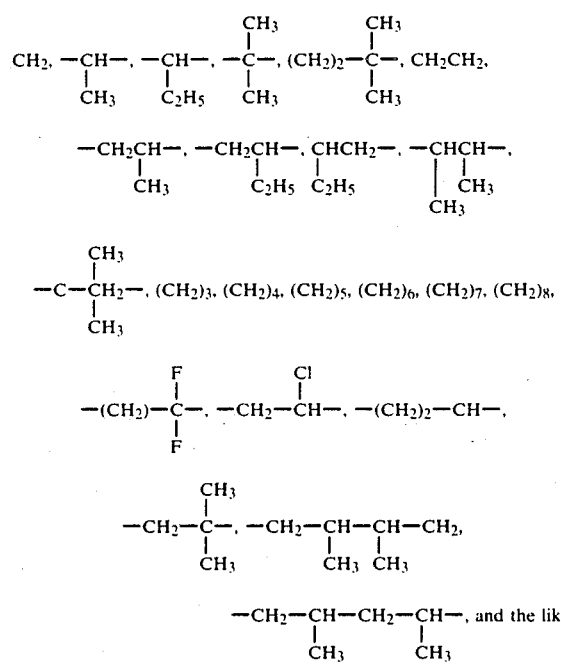

Preferred compounds for use in the method of the invention are those compounds wherein X is CH, m is 0, $R^4$ is H, $R^3$ is H, $R^2$ is in the B ring and is H, OH, halo such as Br or I, alkoxy, such as methoxy, lower alkyl such as n-pentyl, hydroxyalkyleneoxy, such as hydroxybutyleneoxy, alkylthio, such as methylthio, amino, carboxy, alkoxycarbonyl, such as methyloxycarbonyl; and wherein X is CH, m is 0, $R^4$ is H, $R^2$ is in the B ring and is OH or alkoxy, such as methoxy, and $R^3$ is alkyl, such as methyl; wherein X is CH, m is 1, $R^4$ is H, R is H, and $R^2$ is H or OH; and wherein X is N, m is 0, $R^4$ is H and $R^2$ and $R^3$ are H.

The various compounds used in the method of the invention may be prepared as described below.

Thus, to form compounds of formula I employed in the method of the invention wherein $R^3$ is H, and m is 0, starting p-aminophenol compound A

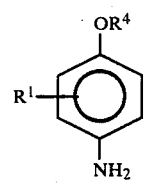

is reacted with compound B

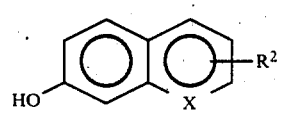

in the presence of aqueous sodium bisulfite in a closed vessel at from about 100° to about 175° C. to form compounds of the structure IV

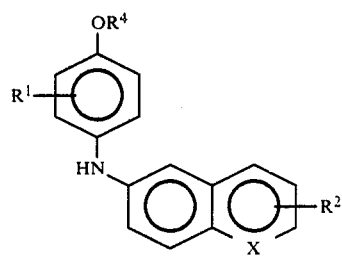

Compounds wherein m is 1 to 5 and $R^3$ is may be prepared by reacting aminophenol A with a compound of the structure C

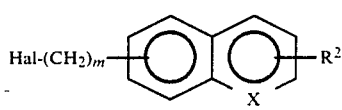

in the presence of weak base such as sodium bicarbonate, and hexamethylphosphoric triamide (HMPA) at temperatures of from about 0° to about 20° C. to form compounds of the structure V

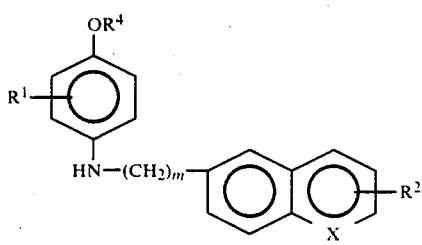

Compounds wherein $R^3$ is alkanoyl or aroyl may be prepared by reacting a compound of structure IV or V with the approximate alkanoyl halide, such as acetyl chloride, or the appropriate aroyl halide, such as benzoyl chloride, in the presence of pyridine and methylene chloride to form compounds of the structure VI

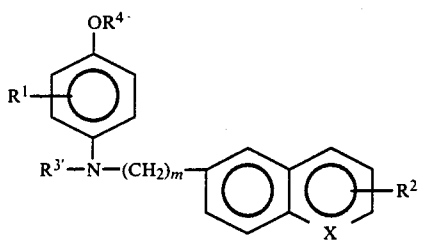

wherein R³' is alkanoyl or aroyl.

Compounds wherein R³ is lower alkyl may be prepared from compounds of formula IV or V. Where R⁴ in the formula IV or V compounds is H, then IV or V is treated with base such as sodium hydride and in the presence of tetrahydrofuran, benzene or ether and then after cessation of H₂ evolution benzyl bromide (or other protecting agent) is added to form the protected compound VII

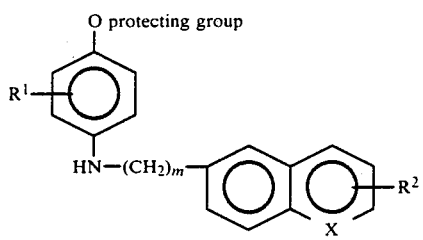

Then, the protected compound VII or the formula IV or V compound wherein R⁴ is other than H is alkylated by reaction with an alkyl halide alkylating agent in the presence of sodium bicarbonate and hexamethylphosphoric triamide at elevated temperatures of from about 20° to about 80° C. to form the alkylated-protected compound VIII

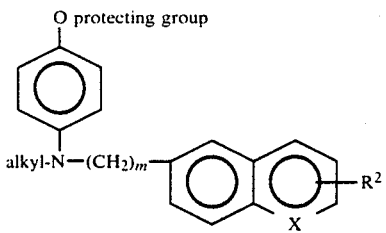

which is then hydrogenated by treatment with H₂ in the presence of palladium on charcoal catalyst in acidic methanol to form the compound IX

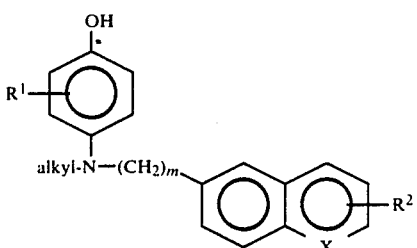

Where R⁴ in the formulae IV or V compounds is other than H, than IV or V may be alkylated directly to form the formula X compound

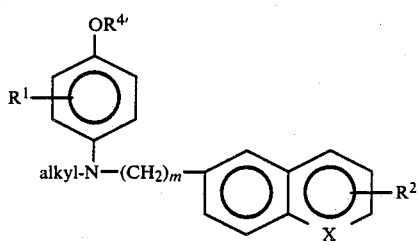

(where R⁴' is alkyl, alkanoyl or aroyl)

The naphthalene derivatives employed as reactants with the aminophenol are commerically available, are known in the literature and/or generally may be prepared by conventional procedures. Thus, the naphthalene reactant B wherein X is CH, that is B'

wherein R² is H, Br or OH at the 6-position are commerically avaliable. Naphthalene reactants wherein R² is Cl, OCH₃ and CO₂H at the 2-position are known in the literature.

Naphthalene reactant B' wherein R² is —O(CH₂)ₙOH may be prepared by starting with the corresponding bromo-2-naphthol C

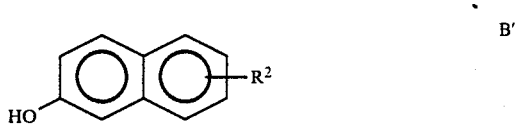

which is dissolved in a dispersion of sodium hydride in tetrahydrofuran, cooled to 0° C. and then treated with alkenyl halide D D CH₂=CH—(CH₂)ₙ₋₂—Hal wherein Hal is Br or Cl naphthalene XI

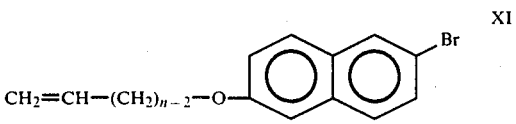

which is dissolved in tetrahydrofuran and then treated with t-C₄H₉Li at reduced temperature of, for example, from about −78° to about −20° C.

After warming to from about −20° C. to about 0° C., a solution of trimethyl borate in tetrahydrofuran is added and then acetic acid and hydrogen peroxide are added to form 2-naphtol derivative XII

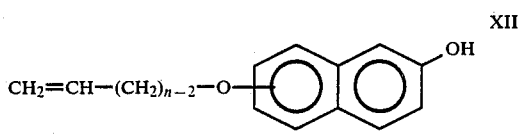   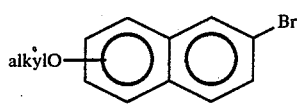

Compound XII in hexane and tetrahydrofuran is treated with borane methyl sulfide complex; thereafter, ethanol, sodium hydroxide and hydrogen peroxide are added to form the 2-naphthalene XIII

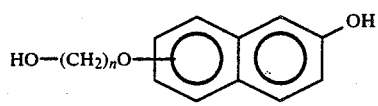

2-Naphthols of the structure XIV

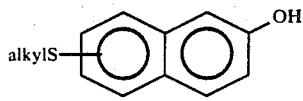

may be prepared by treating bromo-2-naphthol C with sodium hydride in the presence of tetrahydrofuran, and then adding a protecting compound such as bromomethyl methyl ether to form XV

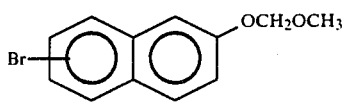

A solution of XV in ether and tetrahydrofuran is cooled to, for example, a reduced temperature of from about −78° to about −60° C. and t-butyllithium is added. Thereafter dialkyldisulfide E is added E  alkylSSalkyl The temperature is maintained at the above reduced temperature for about 30 minutes and then the reaction is warmed to room temperature to form XVI

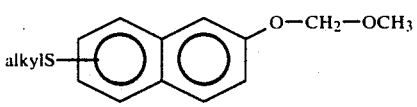

The protecting group is then removed by treating XVI in dioxane with aqueous hydrochloric acid to form XIV.

2-Naphthol compounds wherein $R^2$ is alkoxy may be prepared by treating bromonaphthol C' with sodium hydride

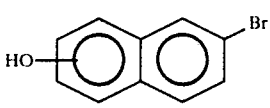

in the presence of tetrahydrofuran and then with an alkyl iodide in the presence of dimethylformamide of form XVII which is then treated sequentially with t-butyllithium in the presence of tetrahydrofuran, then trimethylborate, acetic acid and hydrogen peroxide, as described hereinbefore in the preparation of compound XII to form 2-naphthol compound XVIII

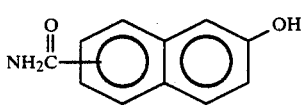

Naphthol XIX wherein $R^2$ is amido, that is

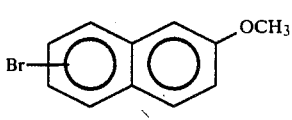

may be prepared by treating bromo-2-methoxynaphthalene, that is

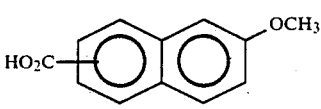

with t-butyllithium in the presence of tetrahydrofuran with $CO_2$ to form XX

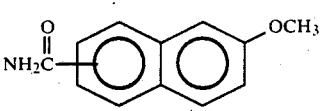

which in solution with dimethylformide and tetrahydrofuan is cooled and treated with oxalyl chloride and ammonium hydroxide to form amino compound XXI

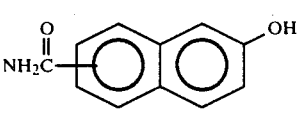

Amino compound is when converted to the 2-naphthol starting material XXII

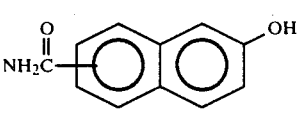

by treating XXI with boron tribromide ($BBr_3$) in the presence of methylene chloride while cooling to a temperature of from about −78° to about 20° C.

The compounds of formulae I, II and III are inhibitors and prevent leukotriene formation in macrophages (Samuelsson, B., Science, Vol. 220, p. 568–575, 1983). The administration of such compounds to humans or animals provides a method for treating allergy of a reagin or non-reagin nature. Asthma is preferably treated but any allergy wherein leukotrienes are thought to be involved as pharmacological mediators of anaphylaxis can be treated. For example, such compounds can be used for treatment of such conditions as allergic rhinitis, food allergy and urticaria as well as asthma.

An effective but essentially non-toxic quantity of the compound is employed in treatment.

The compounds described herein can be administered orally or parenterally, preferably orally, to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in °C. TLC plates were visualized by spraying and heating with 5% phosphomolybdic acid in ethanol.

EXAMPLE 1

4-(2-Naphthalenylamino)phenol

A mixture of 1.00 g (6.94 mmol, Aldrich) of 2-naphthol, 1.01 g (9.26 mmol, Aldrich) of 4-aminophenol, and 5.2 g (50 mmol, Aldrich) of sodium bisulfite in 30 ml of $H_2O$ was refluxed for 36 hours. The reaction mixture was cooled, added to 50 ml of $H_2O$ and extracted with 50 ml of hot ethyl acetate. The organic layer was separated, washed with an additional 50 ml of $H_2O$, dried ($MgSO_4$) and concentrated in vacuo to give a solid. The crude solid was purified by flash chromatography (15×5.0 cm, 1:4 EtOAc/petroleum ether) followed by recrystallization (EtOAc/petroleum ether) to afford 1.15 g (71%) of title compound as pale purple flakes, m.p. 134°–135° C.

IR(KBr) 3401, 1631, 1597, 1515, 1314, 1245, 850, 827, 817, 739 $cm^{-1}$.

270 MHz 1H NMR ($CDCl_3$/DMSO-$d_6$)

6.80 (dd, J=2, 7, 2H)

7.10 (m, 6H)

7.29 (dd, J=7, 8, 1H)

7.5 (d, J=8, 1H)

7.65 (m, 2H)

8.73 (s, 1H)

67.5 MHz $^{13}C$ NMR ($CDCl_3$/DMSO-$d_6$) 105.57, 114.91, 117.84, 120.94, 121.58, 124.76, 125.01, 126.35, 126.69, 127.58, 133.13, 133.80, 142.93, 151.85

MS(CI) 236 $(M+H)^+$

TLC: Rf (silica gel, 1:2 EtOAc/pet ether)=0.44, PMA and UV. The Rf of 2-naphthol under identical conditions was 0.58.

Anal Calcd for $C_{16}H_{13}NO$: C, 81.68; H, 5.57; N, 5.95. Found: C, 81.68; H, 5.69; N, 6.02.

EXAMPLE 2

4-[(6-Methoxy-2-naphthyl)amino]phenol

A. 6-Methoxy-2-naphthol

The procedure used was described in Org. Synthesis, 49, 90 (1969).

The mixture of 590 mg (24.3 mmol, Aldrich) of magnesium turnings and 500 mg (2.11 mmol, Aldrich) of 2-bromo-6-methoxynaphthalene, in 10 ml of dry THF was heated until a reaction began. A solution of 4.50 g (19 mmol) of 2-bromo-6-methoxynaphthalene in 20 ml of THF was added to the reaction mixture over 15 minutes maintaining reflux with external heating when necessary. Refluxing was continued for an additional 30 minutes, then the resulting cooled solution was added dropwise to a solution of 2.6 ml (23 mmol, Alfa) of trimethylborate in 30 ml of dry THF which had been cooled to $-10°$. The reaction temperature was maintained below $-5°$ during the addition. The white slurry which formed was stirred for 15 minutes then 1.8 ml (31 mmol) of glacial acetic acid was added in one portion followed by the dropwise addition of 4.8 ml of 15% aqueous hydrogen peroxide solution. Tee reaction mixture was warmed to room temperature, stirred for 30 minutes then added to 200 ml of 10% aqueous $NH_4Cl$ solution and extracted with 150 ml of ethyl acetate. The organic layer was separated, washed with an additional 150 ml of $H_2O$, dried ($MgSO_4$) and concentrated in vacuo to give a solid. The crude material was purified by flash chromatography (15×5.0 cm, 1:3 EtOAc/pet ether) and then recrystallized (EtOAc/pet ether) to afford 2.45 g (66%) of title alcohol as lusterous white plates, m.p. 145°–147°.

IR (KBr) 3304 (broad), 1609, 1512, 1453, 1388, 1251, 1231, 1155, 1112, 1031, 937, 851, 810 $cm^{-1}$. MS(CI): 175 $(M+H)^+$

B. 4-(6-Methoxy-2-naphthyl)amino]phenol

A mixture of 300 mg (1.72 mmol) of Part A alcohol, 243 mg (2.23 mmol, Aldrich) of 4-aminophenol and 1.00 g (9.6 mmol) of sodium bisulfite in 5.0 ml of $H_2O$ was heated with stirring in a closed tube to 150° for 24 hours. The reaction mixture was cooled, added to 15 ml of ethyl acetate, washed with two 15 ml portions of $H_2O$, dried ($MgSO_4$) and concentrated in vacuo to give a solid. The crude solid was purified by flash chromatography (silica gel, 10×3.0 cm, 1:3 EtOAc/pet ether) then recrystallized (EtOAc/pet ether) to afford 260 mg (57%) of title compound as pink-tinged crystals, m.p. 153°–154°.

IR(KBr) 3417 (broad), 1608, 1508, 1389, 1311, 251, 1231, 1216, 1160, 1024, 853 $cm^{-1}$.

270 MHz $^1H$ NMR ($CDCl_3$+DMSO-$d_6$)

δ3.87 (s, 3H, —$OCH_3$)

6.83 (d, J=8, 2H)

6.90–7.21 (m, 6H)

7.48 (m, 1H)

7.57 (d, J=9, 1H)

15 8.43 (br s, 1H, —NH—)

MS(CI): 266 $(M+H)^+$

TLC:Rf (silica gel, 1:3 EtOAc/pet ether)=0.19, PMA and UV, homogeneous.

Anal Calcd for $C_{17}H_{15}NO_2$: C, 76.96; H, 5.70; N, 5.28. Found: C, 77.00; H, 5.85; N, 5.19.

EXAMPLE 3

6-[(4-Hydroxyphenyl)amino]-2-naphthalenol

A mixture of 300 mg (2.75 mmol, Aldrich) of 4-aminophenol, 1.5 g (90%, 8.4 mmol, Aldrich) of 2,6-dihydroxynaphthalene and 1.0 g (9.6 mmol, Aldrich) of sodium bisulfite in 30 ml of $H_2O$ was refluxed for 18 hours. The reaction mixture was cooled, added to 30 ml of $H_2O$ and extracted with two 25 ml portions of ethyl aetate. The organic extracts were combined, dried ($MgSO_4$), and concentrated in vacuo to give a solid. The crude solid was purified by flash chromatography (15×5.0 cm, 1:2 EtOAc/pet ether) followed by recrystallization (EtOAc/pet ether) to afford 215 mg (31%) of title compound as pale pink crystals, m.p. 195°–196°.

IR(KBr) 3267 (broad), 1608, 1508, 1416, 1377, 1305, 1230, 1150, 1123, 945, 867, 825 cm$^{-1}$.

270 MHz $^1$H NMR (CDCl$_3$+DMSO-d$_6$)
  5.82 (s, 1H, —NH—)
  6.82 (d, J=9, 2, benzene aromatic)
  6.90–7.20 (m, 6H, aromatic)
  7.43 (d, J=8, 1H, naphthalene)
  7.50 (d, J=8, 1H, naphthalene)
  8.30 (s, 1H, —OH)
  8.48 (s, 1H, —OH)
MS(C) 252 (M+H)$^+$ TLC: Rf (silica gel, 1:2 EtOAc/pet ether)=0.14, PMA and UV, homogeneous The Rf of 2,6-dihydroxynaphthalene under identical conditions was 0.27.

Anal Calcd for C$_{16}$H$_{13}$NO$_3$: C, 76.48; H, 5.21; N, 5.57. Found: C, 76.68; H, 5.32; N, 5.65.

EXAMPLE 4

4-[(6-Butoxy-2-naphthalenyl)amino]phenol

A. 2-Bromo-6-butoxynaphthalene

An oil dispersion of 480 mg (50%, 10 mmol, Alfa) of sodium hydride was washed three times with petroleum ether then the residue covered with 5 ml of dry THF. To the resulting stirred slurry was added dropwise a solution of 2.00 g (8.97 mmol, Aldrich) of 6-bromo-2-naphthol, in 10 ml of THF over 10 minutes. The reaction mixture was stirred for 30 minutes then 1.70 g (9.23 mmol, Aldrich) of 1-iodobutane and 15 ml of sieve-dried DMF were added. The resulting solution was heated to 60° for two hours, then cooled, added to 100 ml of $H_2O$ and extracted with 50 ml of petroleum ether. The organic extract was washed with an additional 100 ml of $H_2O$, dried (MgSO$_4$) and concentrated in vacuo to give a solid. The crude material was purified by flash chromatography (15×5 cm, pet ether) to afford 2.31 g (92%) of title compound as a white solid, m.p. 48°–50°.

60 MHz $^1$H NMR (CDCl$_3$)
  0.73–2.20 (m, H, —(CH$_2$)$_2$CH$_3$)
  4.05 (t, J=6, 2H, —OCH$_2$—)
  7.00–8.00 (m, 6H, aromatic)

TLC: Rf (silica gel, 1:9 Et$_2$O/pet ether)=0.63, PMA and UV, homogeneous

B. 6-Butoxy-2-naphthol

To a solution of 500 mg (1.79 mmol) of Part A compound in 10 ml of dry THF at −78° was added 2.0 ml (1.8M in pentane, 3.6 mmol, Aldrich) of t-butyllithium solution over 10 minutes. The reaction mixture was stirred at −78° for 30 minutes, then at −20° for 15 minutes. To the resulting yellow slurry was added dropwise 230 ul (2.0 mmol, Alfa) of trimethylborate. The slurry became homogeneous and after 15 minutes, 114 ul (2.0 mol) of glacial acetic acid was introduced followed by 0.50 ml (~2.2 mmol) of 15% aqueous H$_2$O$_2$. The reaction mixture was allowed to warm to room temperature over ~30 minutes, then added to 30 ml of 1M aqueous HCl solution and extracted with 25 ml of ethyl acetate. The organic extract was washed with an additional 30 ml of 1M aqueous HCl solution, dried (MgSO$_4$) and concentrated in vacuo to give a solid. The crude material was purified by flash chromatography (silica gel, 10×3.0 cm, 1:4 EtOAc/pet ether) to afford 300 mg (78%) of title compound as a white solid, m.p. 100°–102°.

IR(KBr) 3286, 2959, 1610, 1514, 3390, 1254, 1230, 853 cm$^{-1}$.

60 MHz $^1$H NMR (CDCl$_3$)
  0.70–2.1 (m, 7H, —(CH$_2$)$_2$CH$_3$)
  4.00 (t, J=6, 2H, —OCH$_2$—)
  4.78 (s, 1H, —OH)
  6.80–7.80 (m, 6H, aromatic)
MS(CI): 217 (M+H)$^+$ TLC: Rf (silica gel, 1:9 EtOAC/pet ether)=0.15, PMA and UV, homogeneous.

C. 4-[6-Butoxy-2-naphthalenyl)amino]phenol

A mixture of 270 mg (1.25 mmol) of Part B compound 218 mg (2.00 mmol, Aldrich) of 4-aminophnol and 500 mg (4.81 mmol, Aldrich) of sodium bisulfite in 5 ml of 1:4 EtOH/H$_2$O was stirred rapidly in a sealed tube at 170° for 48 hours. The reaction mixture was cooled, added to 25 ml of H$_2$O and extracted with two 20 ml portions of ethyl acetate. The combined organic extracts were dried (MgSO$_4$) and concentrated in vacuo to give a solid. The crude material was purified by flash chromatography (silica gel 9.0×5.0 cm, 1:5 EtOAc/pet ether) followed by recrystallization (ether/pet ether) to afford 160 mg (42%) of title compound as small chalk-white crystals, m.p. 138°–139°.

IR(KBr) 3415, 3290 (broad), 295, 1609, 1512, 1391, 1247, 1189, 1162, 854, 838, 823 cm$^{-1}$.

270 MHz $^1$H NMR(CDCl$_3$)
  0.99 (t, J=7, 3H, —CH$_3$)
  1.53 (tq, J=7,7, 2H, —CH$_2$CH$_3$)
  1.82 (tt, J=7,7, 2H, —OCH$_2$CH$_2$—)
  4.05 (t, J=7, 2H, —OCH$_2$—)
  4.65 (br s, 1H, —OH)
  6.80 (d, J=8, 2H, phenyl protons)
  7.20 (m, 7H, aromatic)
  7.50 (broad d, J=8, 1H, aromatic)
  7.59 (d, J=8, 1H, aromatic)
MS(CI): 308 (M+H)$^+$ TLC: Rf (silica gel, 1:2 EtOAc/pet ether)=0.43, PMA and UV, homogeneous. The Rf of Part B naphthol under similar conditions was 0.60.

Anal Calcd for C$_{20}$H$_{21}$NO$_2$: C, 78.15; H,6.89; N, 4.56. Found: C, 78.13; H, 7.05; N, 4.49.

EXAMPLE 5

4-[6-(Methylthio)-2-naphthalenyl]amino]phenol

A. 6-Bromo-2-methoxymethyleneoxynaphthalene

The oil was removed from 1.2 g (50% in oil, 25 mmol, Alfa) of sodium hydride dispersion by three washes with petroleum ether then 50 ml of dry THF was added to the residue. To the resulting stirred suspension of sodium hydride was introduced in portions a total of 5.00 g (22.4 mmol, Aldrich) of 6-bromo-2-naphthol, over 30 minutes. The reaction mixture was stirred for an additional 30 minute then 2.0 ml (24 mmol, Aldrich) of bromomethyl methyl ether was added dropwise over 15 minutes. After 3 minutes, the reaction mixture was added to 200 ml of $H_2O$ and extracted with two 75 ml portions of ethyl acetate. The organic extracts were combined, dried ($MgSO_4$) and concentrated in vacuo to give a solid. The crude solid was purified by flash chromatography (20×5.0 cm, 1:15 EtOAc/pet ether) to afford 5.55 g (93%) of title compound as a pale yellow solid, m.p. 63°-65°.

IR (KBr) 2958, 1622, 1589, 1497, 1383, 1254, 1200, 1158, 1079, 1000 $cm^{-1}$.

60 MHz $^1$H NMR($CDCl_3$)

5 3.50 (s, 3H, —$OCH_3$)

5.27 (s, 2H, —$OCH_2O$—)

7.02-8.00 (m, 6H, aromatic)

TLC: Rf (silica gel, 1:4 EtOAc/pet ether)=0.53, PMA and UV.

The Rf of 6-bromo-2-naphthol under indentical conditions was 0.26.

B. 6-Methylthio-2-methoxymethyleneoxynaphthalene

To a solution of 2.67 g (10.0 mmol) of Part A compound in 30 ml of dry ether and 10 ml of dry THF at −78° was added dropwise 14 ml (1.4 M in pentane, 20 mmol, Aldrich) of t-butyllithium solution over 20 minutes. The reaction mixture was stirred at −78° for 30 minutes then at −20° for 30 minutes. The resulting slurry was recooled to −78° and 1.1 ml (12 mmol, distilled) of dimethyl disulfide was introduced in one portion. The reaction mixture was stirred at −78° for 30 minutes, warmed to room temperature over 2 hours then added to 50 ml of 1M aqueous NaOH and extracted with 50 ml of ethyl acetate. The organic extract was washed with an additional 50 ml of 1M aqueous NaOH, dried ($MgSO_4$) and concentrated in vacuo to give a yellow solid. The crude material was purified by flash chromatography (15×5.0 cm, 1:20 ether/pet ether) then recrystallized (ether/pet ether) to afford 1.40 g (60%) of title compound as white crystals, m.p. 58°-60°.

IR (KBr) 2967, 1593, 1494, 1380, 1222, 1214, 1194, 1159, 1079, 1070, 993 $cm^{-1}$.

MHz $^1$H NMR ($CDCl_3$)

2.55 (s, 3H, —$SCH_3$)

3.50 (s, 3H, —$OCH_3$)

5.27 (s, 2H, —$OCH_2O$—)

7.07-7.80 (m, 6H, aromatic)

TLC: Rf (silica gel, 1:9 ether/pet ether)=0.38, PMA and UV, co-spots with Part A compound under these conditions.

C. 6-Methylthio-2-naphthol

To a solution of 700 mg (2.99 mmol) of Part B compound in 4 ml of dioxane was added 1 ml of 1M aqueous HCl and heated to 50° for 18 hours. The reaction mixture was cooled, added to 50 ml of $H_2O$ and extracted with two 25 ml portions of ethyl acetate. The organic extracts were combined, dried ($MgSO_4$) and concentrated in vacuo to give a solid. The crude solid was purified by flash chromatography (10×5.0 cm, 1:6 EtOAc/pet ether) to afford 165 mg (29%) of title compound as a white solid, m.p. 120°-122°.

IR(KBr) 3335 (broad), 1599, 1573, 1501, 1432, 1354, 1278, 1210, 916, 863, 856, 813 $cm^{-1}$.

270 MHz $^1$H NMR($CDCl_3$)

2.55 (s, 3H, —$SCH_3$)

4.92 (s, 1H, —OH)

7.10 (m, 2H, aromatic)

7.35 (dd, J=2, 9, 1H, aromatic)

7.60 (m, 3H, aromatic)

MS(CI): 191 $(M+H)^+$

TLC: Rf (silica gel, 1:4 EtOAc/pet ether)=0.37, PMA and UV. The Rf of Part B compound under identical conditions was 0.68.

D. 4-[[6-(Methylthio)-2-naphthalenyl]-amino]phenol

A mixture of 150 mg (0.79 mmol) of Part C naphthol, 170 ml (1.56 mmol, Aldrich) of 4-aminophenol, 500 mg (4.88 mmol, Aldrich) of sodium bisulfite and 5 ml of $H_2O$ was stirred rapidly in a sealed tube at 155°-160° for 60 hours. The reaction mixture was cooled, added to 25 ml of $H_2O$ and extracted with two 25 ml portions of ethyl acetate. The combined organic extracts were dried ($MgSO_4$) and concentrated in vacuo to give a solid. The crude material was purified by flash chromatography (12×3.0 cm, 1:3 EtOAC/pet ether) followed by recrystaliization (EtOAc/pet ether) to afford 149 mg (67%) of title compound as light grey crystals, m.p. 127°-128°. IR(KBr) 3410, 3289 (broad), 1629, 1593, 1518, 1503, 1441, 1311, 1234, 858, 815 $cm^{-1}$.

270 MHz $^1$H NMR($CDCl_3$)

2.54 (s, 3H, —$SCH_3$)

4.58 (s, 1H, —OH)

5.60 (s, 1H, —NH—)

6.82 (d, J=9, 2H, benzene aromatics)

7.09 (d, J=9, 3H, benzene aromatics)

7.14 (d, J=2, 1H)

7.30 (dd, J=2, 9, 1H)

7.50 (d, J=9, 1H)

7.55 (d, J=2, 1H)

7.60 (d, J=9, 1H)

MS(CI): 282 $(M+H)^+$

TLC: Rf (silica gel, 1:3 EtOAc/pet ether)=0.19, PMA and UV, homogeneous.

The Rf of Part C compound under identical conditions was 0.34.

Anal Calcd for C: C, 72.57; H, 5.37; N, 4.98; S, 11.40. Found: C, 72.65; H, 5.20; N, 4.92; S, 11.18.

EXAMPLE 6

4-[[6-[(4-Hydroxyphenyl)amino]-2-naphthalenyl]oxy]-butanol

A. 6-Bromo-2-(2-propenyloxy)naphthalene

A solution of 10.00 g (45 mmol, Aldrich) of 6-bromo-2-naphthol and 2.16 g (49.0 mmol, 1.1 eq. 60% in oil, Aldrich) of NaH dispersion in 100 ml of dry THF was stirred at 0° C., until gas evolution ceased. A solution of 4.60 ml (45.0 mmol, Aldrich) of 4-bromo-1-butene in 25 ml of DMF was added dropwise and the solution was warmed to room temperature, then stirred at 70° C. overnight. To this solution was added 2.28 ml (22.5 mmol, 0.5 eq., Aldrich) of 4-bromo-1-butene and 6 ml of hexamethylphosphoric triamide (HMPA). Then 1.00 g (20.8 mmol, 60% in oil, Aldrich) of NaH dispersion in 10 ml of dry THF was added, stirred at 70° C. for hours and finally heated to 90° C. for 12 hours. The mixture was cooled, water was added, this was extracted with EtOAc, dried ($MgSO_4$) and concentrated in vacuo. Purification was achieved via flash chromatography (silica gel, 1:8 EtOAc/petroleum ether) to yield 4.31 g (35%) of title compound as a bright yellow solid, m.p. 35°-37° C.

IR(KBr) 3474, 3077, 2926, 1627, 1591, 1498, 1459, 1388, 1262, 1207, 1168, 1125, 1064, 1032, 988, 921, 877 cm$^{-1}$

MHz $^1$H NMR(CDCl$_3$)

δ2.61 (dt, J=6, 7 Hz, 2H, —OCH$_2$CH$_2$)
4.12 (t, J=7 Hz, 2H, —OCH$_2$CH$_2$—)
5.18 (m, 2H, —CH=CH—(CH$_2$)$_2$—O—)
5.94 (ddt, J=6, 7Hz, 1H, —CH$_2$=CH—(CH$_2$)$_2$—O—)
7.09 (d, J=3 Hz, 1H, aromatic H)
7.16 (dd, J=3, 9 Hz, 2H, aromatic H's)
7.48 (dd, J=2, 6 Hz, 1H, aromatic H's)
7.58 (d, J=9 Hz, 1H, aromatic H)
7.63 (d, J=9 Hz, 1H, aromatic H)
7.90 (s, 1H, aromatic H)

TLC: Rf (silica gel, 1:1 EtOAc/petroleum ether)=0.78, UV and PMA, homogeneous

B. 6-(2-Propenyloxy)-2-naphthol

To a solution of 5.33 g (19.2 mmol) of Part A compound in 20 ml of dry THF at −78° C. was added 23.3 ml (42.3 mmol, 2.2 eq., 1.82 M in pentane, Aldrich) of t-BuLi over 20 minutes. After 30 minutes, the solution was warmed to −20° C., stirred for 15 minutes then a solution of 2.40 ml (23.0 mmol, 1.2 eq., Alfa) of trimethylborate in 5 ml of dry THF was added. After 15 minutes, 1.7 ml (29 mmol) of glacial acetic acid was added, followed by 2.30 ml (23.0 mmol, 1.2 eq.) of 30% aqueous H$_2$O$_2$ in 3 11 of H$_2$O. The resulting mixture was warmed to room temperature and stirred for 30 minutes To this was added 10% aqueous NH$_4$Cl and this was extracted with EtOAc. The organic layer was washed with H$_2$O, dried (MgSO$_4$) and concentrated in vacuo. Purification was accomplished via flash chromatography (silica gel, 1:6, 1:8 EtOAc/petroleum ether) and washing with petroleum ether to afford 2.04 g (50%) of title compound as lustrous white crystals: m.p. 92°-93° C.

IR(KBr) 3262, 1607, 1513, 1388, 1233, 1155, 1113, 1032, 951, 916, 852, 810 cm$^{-1}$.

270 MHz $^1$H NMR(CDCl$_3$)

62.60 (dt, J=5, 5 Hz, 2H, —OCH$_2$CH$_2$—)
4 11 (t, J=5 Hz, 2H, OCH$_2$CH$_2$—)
4.86 (s, 1H, —OH)
5.12 (m, 2H, CH$_2$=CH—)
5 94 (ddt, J=6, 5, 3 Hz, 1H, CH$_2$=CH—)
7.06 (m, 4H, aromatic H's)
7 56 and 7.63 (two d's overlapping, J=6 Hz, 2H, aromatic H's)

MS(CI): 215 (M+H)$^+$

TLC: Rf (silica gel, 1:1 EtOAc/petroleum ether)=0.61, UV and PMA, homogeneous.

C. 6-(4-Hydroxybutoxy)-2-naphthol

A solution of 720 mg (3.4 mmol) of Part A compound in 5 ml of hexanes and 2 ml of dry THF was cooled to 0° and 0.14 ml (10 M, 0.4 eq., 1.4 mmol, Aldrich) of borane methyl sulfide complex was added. The resulting slurry was warmed to room temperature and stirred. During 1 hour, an additional 2 ml of dry THF and 70 μl (10 M, 0.7 mmol, Aldrich) of borane methyl sulfide complex were added. After 1.5 hours, another 70 ul (0.2 eq., 10 M, 0.7 mmol, Aldrich) of borane methyl sulfide complex was added. After one hour, 2 ml of EtOH was added, followed by 2 ml of 3N NaOH and then the solution was cooled to 0° C. To this was slowly added 700 μl (7.2 mmol, 11.05 eq.) of 30% aqueous H$_2$O$_2$ and the solution was refluxed for 1 hour. The solution was cooled, EtOAc was added and this was washed with brine, dried (MgSO$_4$) and concentrated in vacuo. The aqueous layers were acidified using concentrated HCl, combined and then extracted with EtOAc. The organic layers were combined, dried (MgSO$_4$) and concentrated in vacuo. Final purification was achieved via flash chromatography (silica gel, 1:4, 1:2 EtOAc/petroleum ether) to yield 289 mg (37%) of title compound as a white solid, m.p. 148°-150° C.

IR(KBr) 3365, 3084, 2951, 1605, 113, 1445, 1391, 1228, 1158, 1050, 961, 863, 853, 806 cm$^{-1}$

270 MHz $^1$H NMR(CDCl$_3$)

δ1.75 (dt, J=7, 7 Hz, 2H, HOCH$_2$CH$_2$—)
1.85 (dt, J=7, 7Hz, 2H, —CH$_2$CH$_2$OR)
3.71 (t, J=7 Hz, 2H, —CH$_2$OH)
4.08 (t, J7 Hz, 2H, —CH$_2$CH$_2$OR)
7.07 (m, 4H, aromatic H's)
7.57 (t, J=Hz, 2H, aromatic H's)

TLC: Rf (silica gel, 1:1 EtOAc/petroleum ether)=0.21, U and PMA.

D. 4-[[6-[(4-Hydroxyphenyl)amino)-2-naphthalenyl]oxy]-butanol

A rapidly stirred solution of 290 mg (1.3 mmol) of Part B compound, 283 mg (2.60 mmol, 2 eq., Aldrich) of 4-aminophenol and 500 mg (4.8 mmol, 3.7 eq.) of sodium bisulfite in 5 ml of H$_2$O was heated in a sealed tube to 150° C. for 19 hours. The solution was cooled, water was added and this was extracted with EtOAc. The organic layers were combined, dried (MgSO$_4$) and concentrated in vacuo. Initial purification was accomplished via flash chromatography (silica gel, 2, THF/petroleum ether). The resulting product contaminated with Part C compound was washed with 0.N NaOH, followed by H$_2$O. Final purification via flash chromatography (1:3 THF/petroleum ether) yielded 180 mg (43%) of title compound as a light purple solid, m.p. 132°-135° C.

IR(KBr) 3421, 2947, 1608, 1509, 1389, 1316, 1249, 1163, 1047, 1003, 952, 857, 818 cm$^{-1}$

270 MHz 1H NMR(DMSO-d$_6$)

δ1.60 (dt, J=6, 6 Hz, 2H, —CH$_2$CH$_2$OH))
1.78 (dt, J=6, 6 Hz, 2H, -OCH$_2$CH$_2$—)
3.47 (dt, J=6, 6 Hz, 2H, —CH$_2$OH)
4.02 (t, J=6 Hz, 2H, —OCH$_2$CH$_2$—)
4.43 (t, J=6 Hz, 1H, —CH$_2$OH)
6.72 (d, J=8 Hz, 2H)
7.00 (d, J=8 Hz, 3H)
7.13 (m, 3H)
7.50 (d, J=9 Hz, 1H)
7.59 (d, J=8 Hz, 1H)
8.97 (s, 1H, —OH or NH)

MS(CI): 324 (M+H)$^+$

TLC: Rf (silica gel, 1:1 EtOAc/petroleum ether)=0.36, UV and PMA, homogeneous.

Anal Calcd for C$_{20}$H$_{21}$NO$_3$: C, 74.28; H, 6.55; N, 4.33. Found: C, 73.99; H, 6.55; N, 4.35.

EXAMPLE 7

6-[(4-Methoxyphenyl)amino]-2-naphthalenol

A solution of 1.00 g (8.1 mmol, Aldrich) of p-anisidine, 5.20 g (32.5 mmol, 4 eq., Aldrich) of 2,6-dihydronaphthalene and 3.38 g (32.5 mmol, eq., Aldrich) of sodium bisulfite in 60 ml of H$_2$O was refluxed for 12 hours. The reaction was cooled to room temperature, extracted with EtOAc, dried (MgSO$_4$) and concentrated in vacuo. Initial purification was accomplished via flash chromatography (1:6, 1:4 EtOAc/petroleum ether) and then concentration of appropriate fractions. Ethyl acetate was added, this was washed repeatedly with warm 0.1 N NaOH to remove 2,6-dihydroxynaphthalene, dried (MgSO4) and concentrated n vacuo. Final purification by flash chromatography (1:4 THF/petroleum ether) yielded 633 mg (30%) of title compound as a muddy pink solid, m.p. 152°–153° C.

IR(KBr) 3419, 3374, 1610, 1504, 1318, 1267, 1227, 1183, 1148, 1125, 1023, 946, 866 cm$^{-1}$.

270 MHz $^1$H NMR (CDCl$_3$ +CD$_3$OD)
- 3.80 (s, 3H, OCH$_3$)
- 6.87 (d, J=9 Hz, 2H, aromatic H's)
- 7.01–7.12 (m, 5H, aromatic H's)
- 7.2 (s, 1H, aromatic H's)
- 7.48 (d, J=8 Hz, 1H, aromatic H's)
- 7.53 (d, J=9 Hz, 1H, aromatic H's)

MS(CI): 266 (M+H)$^+$.

TLC: Rf (silica gel, 1:1 EtOAc/petroleum ether)=0.50, UV and PMA, homogeneous

Anal Calcd for C17H : C, 76.96; H, 5.71; N, 5.28.
Found: C, 76.74; H, 5.86; N, 5.22.

EXAMPLE 8

6-[(4-(Hydroxyphenyl)amino]naphthalene-2-amide

A. 6-Methoxy-2-naphthalene carboxylic acid

A solution of 8.00 g (33.8 mmol, Aldrich) of 6-bromo-2-methoxynaphthalene in 75 ml of dry THF was cooled to −78° C. and 36 ml (1.8M in pentane, 65 mmol, Aldrich) of t-butyllithium was added over 30 minutes. The reaction mixture was stirred for 30 minutes at −78° C. then warmed to −20° C. for 30 minutes. The mixture was recooled to −78° C. and 8.00 g (180 mmol) of crushed dry ice was added to the slurry, and then this was allowed to warm to room temperature over 2 hours. The mixture was concentrated in vacuo, 100 ml of 1N HCl was added to the residue and this was extracted with 100 ml of hot EtOAc. The organic layer was washed with water, dried (MgSO4) and concentrated in vacuo to give a solid. Purification via recrystallization (EtOAc/petroleum ether) afforded 5.80 g (85%) of the title compound as small white needles: m.p. 198°–200° C.

IR(KBr) 3449, 2968, 2941, 1683, 1626, 1483, 1300, 1257, 1209, 1031, 860 cm$^{-1}$.

270 MHz $^1$H NMR(DMSO-d$_6$)
- δ3.91 (s, 3H, -OCH$_3$)
- 7.24 (d, J=9 Hz, 1H, aromatic H)
- 7.39 (s, 1H, aromatic H)
- 7.90 (dd, J=8, 8 Hz, 2H, aromatic H's)
- 8.01 (d, J=9 Hz, 1H, aromatic H)
- 8.51 (s, 1H, aromatic H)

TLC: Rf (1:1 EtOAc/petroleum ether)=0.37, UV and PMA.

B. 6-Methoxy-2-naphthaleneamide

A solution of 750 mg (3.71 mmol) of Part A compound and 3 drops of DMF in 10 ml of dry THF was cooled to 0° C., then 490 ul (5.60 mmol, 1.5 eq., Aldrich) of oxalyl chloride was slowly added. After 45 minutes the reaction mixture was slowly added to 10 ml of 10% aqueous NH4OH at 0° C., then the solution was warmed to room temperature and stirred for 2 hours. To this was added 1N aqueous HCl, and extracted with warm EtOAc. The organic layers were warmed, filtered through a small pad of MgSO4 and concentrated in vacuo. Purification via recrystallization. (EtOAc-/EtOH/petroleum ether) afforded 480 mg (64%) of title compound as white lustrous needles: m.p. 224°–226° C.

IR(KBr) 3379, 3198, 1656, 1627, 1599, 1484, 1391, 1263, 1220, 1030, 916, 863, 818 cm$^{-1}$.

270 MHz $^1$H NMR (DMSO-d$_6$)
- δ3.90 (s, 3H, —OCH$_3$)
- 7.23 (d, J=Hz, 1H, aromatic H)
- 7.37 (m, 2H, aromatic H's, amide H)
- 7.87 (m, 4H, aromatic H's, amide H)
- 8.40 (s, 1H, aromatic H)

TLC: Rf (1:9 MeOH/CH$_2$Cl$_2$)=0.34, UV only.

C. 6-Hydroxy-2-naphthaleneamide

A solution of 470 mg (2.34 mmol) of Part B compound in 5 ml of dry CH$_2$Cl$_2$ was cooled to −78° C. and 2.60 ml (1M in CH$_2$Cl$_2$, Aldrich, 2.60 mmol) of BBr$_3$ was added. The solution was warmed to room temperature, stirred for 2.5 hours then re-cooled to −78° C. To this solution was added another 2.60 ml (1M in CH$_2$Cl$_2$, Aldrich, 2.60 mmol) of BBr$_3$ then warmed to 0° C., stirred for 15 minutes and finally warmed to room temperature. The solution was stirred for 12 hours at room temperature, then slowly poured into 50 ml of saturated aqueous NaHCO$_3$ and extracted with two 30 ml portions of EtOAc. The organic layers were combined, washed with H$_2$O, then brine, dried (MgSO$_4$) and concentrated in vacuo. Purification was achieved via recrystallization (EtOAc/petroleum ether) to yield 343 mg (78%) of title compound as a yellow solid: m.p. 205°–206° C.

IR(KBr) 3403, 3217, 1648, 1602, 1485, 1298, 1221, 1157, 924, 871, 817 cm$^{-1}$.

270 MHz $^1$H NMR(DMSO-d$_6$)
- δ7.13 (d, J=8 Hz, 2H, aromatic H's)
- 7.26 (s, 1H, —NH—)
- 7.69 (d, J=8 Hz, 1H, aromatic H)
- 7.83 (d, J=8 Hz, 2H, aromatic H's)
- 7.95 (s, 1H, —NH—)
- 8.33 (s, 1H, aromatic H)
- 9.44 (s, 1H, —OH)

TLC: Rf (1:9 MeOH/CH$_2$Cl$_2$)=0.19 UV and PMA.

D. 6-[(4-(Hydroxyphenyl)amino]naphthalene-2-amide

A solution of 320 mg (1.71 mmol) of Part C compound, 373 mg (3.42 mmol, 2 eq., Aldrich) of 4-aminophenol and 0.5 g (4.8 mmol) of sodium bisulfite in 5 ml of H$_2$0 was heated to 150° C. in a sealed tube for 17 hours. Then another 373 mg (3.42 mmol, 2 eq., Aldrich) of 4-aminophenol was added and heating at 150° C. in a sealed tube was continued for 16 hours. The solution was cooled, added to H$_2$O and this solution was extracted with EtOAc. The organic layers were combined, washed with brine, dried (MgSO$_4$) and concentrated in vacuo. Purification via flash chromatography (silica gel, 2:3 THF/petroleum ether) then recrystallization (aqueous MeOH) afforded 129 mg (27%) of title compound as an orange solid: m.p. 260° C. IR(KBr) 3437, 3197, 1668, 1626, 1592, 1512, 1497, 1402, 1321, 1241, 1170, 1145, 1104, 812 cm$^{-1}$.

270 $^1$H NMR(DMSO-d$_6$)
- δ6.48 (s, 1H, amine—NH—or —OH)
- 6.77 (d, J=8 Hz, 2H, phenol H's)
- 7.13 (m, 4H, aromatic H's, amide H, phenol H's)
- 7.56 (d, J=9 Hz, 1H, aromatic H's)
- 7.75 (m, 2H, aromatic H's)
- 7.90 (br s, 1H, amide H)
- 8.13 (s, 1H, aromatic H)
- 8.26 (s, 1H, aromatic H)

9.13 (s, 1H, amine NH or —OH)
MS(CI): 279 (M+H)[1]
TLC: Rf (silica gel, 1:9 MeOH/CH$_2$Cl$_2$)=0.17, UV and PMA, homogeneous.
Anal Calcd for C17H : C, 73.37; H, 5.07; N, 10.06.
Found: C, 73.13; H, 5.06; N, 9.82.

EXAMPLE 9

6-[(4-Hydroxyphenyl)amino]-2-naphthalenecarboxylic acid, methyl ester

A. 6-Hydroxy-2-naphthalene carboxylic acid

To a slurry of 5.00 g (2.4 mmol, Aldrich) of 6-bromo-2-naphthol in 150 ml of dry ether at −78° was added dropwise, 16 ml (1.4M in ether, 22 mmol, Aldrich) of methyllithium solution over 10 minutes. The reaction mixture was stirred for 10 minutes, then 28 ml (1.8M in pentane, 50 mmol, Aldrich) of t-butyllithium solution was added dropwise over 15 minutes. The resulting slurry was stirred at −78° for 30 minutes then at 0° for 15 minutes. The reaction mixture was re-cooled to −78°, added into 100 g of crushed dry ice via cannula, and allowed to warm to room temperature over about ~2 hours, then added to 200 ml of 1M aqueous HCl solution and extracted with 100 ml of ethyl acetate. The organic extract was separated, washed with an additional 200 ml of H$_2$O and concentrated in vacuo to give a pale yellow solid. The crude material was dissolved in 125 ml of warm, saturated aqueous NaHCO$_3$ solution and extracted with two 50 ml portions of ethyl acetate. The aqueous phase was acidified to pH 1 with concentrated HCl. The solid which precipitated was collected on a Buchner funnel then dried under vacuum at 110° to afford 2.95 g (70%) of title compound as an off-white powder, m.p. 237°–241°.

IR(KBr) 3429 (broad, 1669, 1626, 1484, 1396, 1289, 1206 cm$^{-1}$.
270 MHz $^1$H NMR(CDCl$_3$+DMSO-d$_6$)
 7.17 (m, 2H)
 7.65 (d, J=8, 1H)
 7.79 (d, J=10, 1H)
 7.92 (dd, J=2, 9, 1H)
 8.46 (s, 1H)
 9.62 (br s, 1H, —OH)
Partial 67.5 $^{13}$C NMR(CDCl$_3$/DMSO-d$_6$) 156.49, 167.37.
MS(CI): 189 (M+H)$^+$
TLC Rf (silica gel, 1:9 MeOH/CH$_2$CL$_2$)=0.55, UV.

B. 6-[(4-Hydroxyphenyl)amino]]-2-naphthalene carboxylic acid, methyl ester

A mixture of 300 mg (1.60 mmol) of Part A compound, 218 mg (2.00 mmol, Aldrich) of 4-aminophenol and 500 mg (4.80 mmol, Aldrich) of sodium bisulfite in 5 ml of H$_2$O was heated to 150° with rapid stirring in a sealed Pyrex tube for 24 hours. The reaction mixture was cooled, added to 50 ml of H$_2$O and extracted with 50 ml of ethyl acetate. The organic extract was separated, washed with an additional 50 ml of H$_2$O and dried (MgSO$_4$). The resulting solution was cooled in an ice-bath and treated with excess ethereal diazomethane. After 5 minutes, 1 ml of glacial acetic acid was added and the solution concentrated in vacuo to give a yellow oil. The crude oil was purified by flash chromatography (10 ×5.0 cm. 1:4 EtOAc/petroleum ether) followed by recrystallization (ether/petroleum ether) to afford 360 mg (77%) of title ester as yellow crystals, m.p. 174°–175°.

IR(KBr) 3393(broad), 1691, 1626, 1508, 1301, 1270, 1209, 824 cm$^{-1}$.
270 MHz $^1$H NMR(CDCl$_3$ +DMSO-d$_6$)
 3.92 (s, 3H, —OCH$_3$)
 6.69 (s, 1H)
 6.87 (d, J=9, 2H, benzene aromatics)
 7.05 (m, 4H)
 7.51 (d, J=9, 1H)
 7.72 (d, J=9, 1H)
 7.87 (dd, J=2, 9, 1H)
 8.39 (s, 1H, —NH—or —OH)
 8.66 (s, 1H, —NH—or —OH)
67.5 MHz 13C NMR(CDCl$_3$+DMSO-d$_6$) 51.44, 105.57, 115.84, 118.71, 122.87, 123.76, 125.29, 125.43, 126.16, 130.09, 130.40, 132.63, 137.18, 146.11 153.47, 167.09.
MS(CI): 294 (M+H)$^+$
TLC: Rf (silica gel, 1:2 EtOAc/petroleum ether)=0.27, PMA and UV, homogeneous
Anal Calcd for C$_{18}$H$_{15}$No$_3$: C, 73.71; H, 5.15; N,44.78.
Found: C, 73.63; H, 5.14; N, 4.67.

EXAMPLE 10

6-[(4-Hydroxyphenyl)amino]-2naphthalene carboxylic acid

A. 6-[(4-Hydoxyphenyl)amino]-2-naphthalene carboxylic acid, phenylbenzyl ester In a sealed thick-walled tube a rapidly stirred mixture of 300 mg (1.60 mmol)of Example 9, Part A acid, 220 mg (2.02 mmol, Aldrich) of 4-aminophenol and 500 mg (4.8 mmol, Aldrich) of sodium bisulfite in 5 ml of H$_{20}$ was heated to 150° C. for 25 hours. The reaction mixture was cooled, added to 50 ml of H$_2$O and extracted with two 30 ml portions of hot ethyl acetate. The organic extracts were combined, dried (MgSO$_4$) then 400 mg (2.06 mmol) of diphenyldiazomethane was added. The resulting purple solution was kept at room temperature for 7 days and finally concentrated in vacuo to give an oil. The crude oil was purified by flash chromatography (15×5.0 cm, 1:2 EtOAc/petroleum ether) to afford 530 mg (74%) of title ester as a yellow foam.

IR(KBr) 3393, 1691, 1624, 1510, 1279, 1232, 1197, 1096 cm$^{-1}$.
60 MHz $^1$H NMR(CDCl$_3$)
 5.47 (br s, 1H, —NH—)
 5.78 (s, 1H, benzylic methine)
 66.80–8.25 (m, 20H, aromatic)
 8.55 (s, 1H, —OH)
MS(CI): 446 (M+H)$^+$
TLC: Rf (silica gel, 1:2 EtOAc/petroleum ether)=0.25, PMA and UV
The Rf of the ester of Example 9, Part A acid under identical conditions was 0.38, UV only.

B. 6-[(4-Hydroxyphenyl)amino]-2-naphthalene carboxylic acid

A mixture of 450 mg (1.01 mmol) of Part A compound and 100 mg of 10% Pd/C catalyst in 1 ml of methanol was stirred rapidly under an atmosphere of hydrogen (balloon) for 18 hours then filtered through a plug of silica gel. The filtrate was concentrated in vacuo to give a solid. The crude solid was purified by flash chromatography (10×3.0 cm, 1:4 EtOAc/petroleum ether then 1:1 EtOAc/petroleum ether containing 1% MeOH) to afford 175 mg (62%) of title compound as a lavender solid, m.p. 252° (dec.).

IR (KBr) 3196 (broad), 1678, 1624, 1513, 1495, 1324, 1266, 1233, 1197 cm$^{-1}$.

270 MHz $^1$H NMR(DMSO-d$_6$)

6.77 (d, J=9, 2H, benzene ring)
7.08 (d, J=9, 2H, benzene ring)
7.12 (s, 1H)
7.17 (d, J=9, 1H)
7.57 (d, J=9, 1H)
7.76 (d, J=8, 1H)
7.83 (d, J=9, 1H)
8.22 (s, 1H)
8.33 (s, 1H)

MS(CI): 280 (M+H)+

TLC: Rf (silica gel, 1:9 MeOH/CH$_2$Cl$_2$)=0.33, PMA and UV, homogeneous

The Rf of Part A compound under indentical conditions was 0.70.

Anal Calcd for C$_{17}$H$_{13}$NO$_3$: C, 73.11; H, 4.69; N, 5.02. Found: C, 72.57; H, 4.84; N, 4.93.

EXAMPLE 11

4-[(6-Pentyl-2-naphthalenyl)amino]phenol

A. 6-(1-Hydroxypentyl)-2-naphthol

To a solution of 1.00 g (4.48 mmol, Aldrich) of 6-bromo-2-naphthol in 40 ml of dry ether at −78° was added dropwise 3.2 ml (1.4M in ether, 5.0 mmol) of methyllithium solution. The reaction mixture was stirred for 5 minutes then 5.0 ml (1.8M in pentane, 9.0 mmol) of t-butyllithium solution was added over 5 minutes. The resulting slurry was stirred at −78° C. for 30 minutes then at 0° for 15 minutes, re-cooled to −78° and a solution of 0.50 ml (4.7 mmol) of distilled valeraldehyde in 3 ml of ether was added dropwise over several minutes. After 5 minutes the reaction mixture was warmed to 0°, quenched with 1 ml of H$_2$O, added to 100 ml of ice-cold saturated aqueous NH$_4$Cl solution. The organic layer was separated, washed with 100 ml of H$_2$O, dried (MgSO$_4$) and concentrated in vacuo to give a dark oil. The crude oil was purified by flash chromatography (10×5.0 cm, 1:3 EtOAc/petroleum ether) to afford 590 mg (57%) of title compound as a pale yellow solid, m.p. 109°-111°.

60 MHz $^1$H NMR(CDCl$_3$/CD$_3$OD)

δ0.80 (crude t, 3H, —CH$_3$)
1.03-2.20 (m, 6H, —(CH$_2$)$_3$CH$_3$)
3.72 (br s, 2H, —OH)
4.73 (t, J=6, 1H, benzylic methine)
6.90-7.83 (m, 6H, aromatic)

TLC: Rf (silica gel, 1:2 EtOAc/petroleum ether)=0.29, PMA and UV. The Rf of 6-bromo-2-naphthol under identical conditions was 0.53.

B. 6-Pentyl-2-naphthol

To a slurry of 500 mg (2.17 mmol) of Part A compound in 3 ml of triethylsilane (Aldrich) was added 33 ml of trifluoroacetic acid dropwise at room temperature. The reaction mixture was stirred for 30 minutes then concentrated in vacuo to give a solid. The crude solid was washed with petroleum ether then purified by flash chromatography (silica gel, 10×3 cm, 1:5 EtOAc/petroleum ether) and recrystallized (benzene/petroleum ether) to afford 435 mg (94%) of title compound as white crystals, m.p.94°-95°.

IR(KBr) 3287, 2851, 1642, 1609, 1510, 1467, 1453, 1288, 1228, 1157 cm$^{-1}$.

270 MHz $^1$H NMR(CDCl$_3$)

δ0.89 (t, J=7, 3H, —CH$_3$)
1.34 (m, 4H, —(CH$_2$)$_2$CH$_3$)
1.68 (m, 2H, —CH$_2$(CH$_2$)$_2$CH$_3$)
2.72 (t, J=8, 2H, benzylic —CH$_2$—)
4.83 (s, 1H, —OH)
7.06 (dd, J=3, 9, 1H)
7.11 (d, J=2, 1H)
7.28 (dd, J=2, 9, 1H)
7.53 (s, 1H)
7.59 (d, J=8, 1H)
7.67 (d, J=8, 1H)

MS(CI): 215 (M+H)+

TLC: Rf (silica gel, 1:3 EtOAc/petroleum ether)=0.46, UV and PMA; the Rf of Part A compound under identical conditions was 0.17.

C. 4-[(6-Pentyl-2-naphthalenyl)amino]phenol

A mixture of 25 mg (1.29 mmol) of Part B compound, 185 mg (1.70 mmol, Aldrich) of 4-aminophenol and 1.00 g (9.6 mmol, Aldrich) of sodium bisulfite in 6 ml of 1:2 dioxane/water was heated to 150° with rapid stirring in a closed tube for 48 hours. The reaction mixture was cooled, added to 25 ml of H$_2$O and extracted with 25 ml of ethyl acetate. The organic extract was washed with 25 ml of H$_2$O, dried (MgSO$_4$) and concentrated in vacuo to give a solid. The crude material was purified by flash chromatography (silica gel, 12×3.0 cm, 1:5 EtOAc/petroleum ether) then recrystallized (EtOAc/petroleum ether) to afford 48 mg (12%) of title compound as white crystals, m.p. 134°-135°.

IR(KBr) 3402, 2924, 1633, 1608, 1516, 1315, 1252, 870, 817 cm$^{-1}$.

270 MHz $^1$H NMR(CDCl$_3$)

δ0.89 (t, J=7, 3H, —CH$_3$)
1.34 (m, 4H, —(CH$_2$)$_2$CH$_3$)
1.68 (m, 2H, —CH$_2$(CH$_2$)$_2$CH$_3$)
2.70 (t, J=7, 2H, benzylic methylene)
4.54 (br s, 1H, —OH or NH)
5.57 (br s, 1H, —OH or NH)
6.81 (d, J=9, 2H, aromatic)
7.00-7.30 (m, 5H, aromatic)
7.48 (s, 1H, aromatic)
7.51 (d, J=8, 1H, aromatic)
7.63 (d, J=8, 1H, aromatic)

MS(CI): 306 (M+H)+

TLC: Rf (silica gel, 1:3 EtOAc/petroleum ether)=0.26, PMA and UV, homogeneous. The Rf of Part B compound under identical conditions was 0.48.

Anal Calcd for C$_{21}$H$_{23}$NO: C, 82.58; H, 7.59; N, 4.59. Found: C, 82.70; H, 7.61; N, 4.27.

EXAMPLE 12

4-[(6-Bromo-2-naphthalenyl)amino]phenol

A mixture of 334 mg (1.50 mmol, Aldrich) of 6-bromo-2-naphthol, 218 mg (2.00 mmol, Aldrich) of 4-aminophenol, and 1.0 g of sodium bisulfite in 5 ml of H$_2$O was heated to 150° in a closed Pyrex tube for 76 hours. The reaction was cooled, added to 25 ml of H$_2$O and extracted with 25 ml of ethyl acetate. The organic extract was dried (MgSO$_4$) and concentrated in vacuo to give a solid. The crude solid was purified by flash chromatography (10×5.0 cm, 1: EtOAc/petroleum ether) followed by recrystallization (EtOAc/petroleum ether) to afford 330 mg (70%) of title compound as small grey-white crystals, m.p. 179°-180°.

IR(KBr) 3405 (broad), 1627, 1590, 1525, 1315, 1251, 869, 815 cm$^{-1}$.

270 MHz $^1$H NMR (CDCl$_3$/DMSO-d$_6$)

δ 6.06 (s, 1H, —NH—)
6.86 (m, 2H)
7.08 (m, 4H)
7.39 (m, 2H)
7.56 (d, J=8, 1H)
7.80 (s, 1H)
8.40 (s, 1H, —OH)
MS(CI): 314, 316 (M+H)+

TLC: Rf (silica gel, 1:4 EtOAc/petroleum ether)=0.12, PMA and UV. The Rf of 6-bromo-2-naphthol under identical conditions was 0.25.

Anal Calcd for $C_{16}H_{12}BrNO$: C, 61.17; H, 3.85; N, 4.46; Br, 25.43. Found: C, 61.13; H, 3.84; N, 4.38; Br, 25.42.

EXAMPLE 13

4-[(6-Iodo-2-naphthalenyl)amino]phenol

A. 6-Iodo-2-methoxynaphthalene

To a solution of 1.00 g (4.22 mmol, Aldrich) of 6-bromo-2-methoxynaphthalene in 10 ml of dry THF at -78° was added dropwise 4.5 ml (1.4M in pentane, 6.3 mmol, Aldrich) of t-butyllithium solution over 10 minutes. The reaction mixture was stirred at −78° for 30 minutes then at 0° for 15 minutes. The resulting yellow solution was re-cooled to −78° then 1.20 g (4.72 mmol, Aldrich) of iodine was added in one portion. The reaction mixture was warmed to room temperature, stirred for 1 hour then added to 50 ml of $H_2O$ and extracted with 50 ml of ethyl acetate. The organic extract was washed with an additional 50 ml of $H_2O$, dried ($MgSO_4$) and concentrated in vacuo to give a solid. The crude solid was recrystallized (EtOAc/petroleum ether) to afford 805 mg (67%) of title compound as pale yellow flakes, m.p. 142°-143°.

IR(KBr) 1622, 1578, 1494, 1264, 112, 1165, 1029, 898, 854, 817, 476, 465 cm$^{-1}$.

270 MHz $^1$H NMR(CDCl$_3$)
3.89 (s, 3H, —OCH$_3$)
7.05 (d, J=3, 1H)
7.12 (dd, J=3, 9, 1H)
7.45 (d, J=8, 1H)
7.59 (d, J=9, 1H)
7.64 (dd, J=2, 8, 1H)
8.11 (s, 1H)

7.5 MHz $^{13}$C NMR·(CDCl$_3$) 55.32, 88.05, 105.8, 19.5, 128.4 (s), 130.6, 133.4, 134.8, 136.3, 158.0.

MS(CI): 285 (M+H)+

TLC: Rf (silica gel, 1:4 ether/petroleum ether)=0.49, UV and PMA, homogeneous.

The Rf of 6-bromo-2-methoxynaphthalene under identical conditions was 0.58.

B. 6-Iodo-2-naphthol

To a solution of 475 mg (1.67 mmol) of Part A compound in 10 ml of dry $CH_2Cl_2$ at −78° was added 2.0 ml (1.0M in $CH_2Cl_2$, 2.0 mmol, Aldrich) of boron tribromide solution. The reaction mixture was allowed to warm to room temperature, stirred for 2 hours then added to 50 ml of saturated aqueous $NaHCO_3$ solution and extracted with 35 ml of ethyl acetate. The organic layer was separated, washed with 25 ml of $H_2O$, dried ($MgSO_4$) and concentrated in vacuo to give a solid. The crude material was purified by flash chromatography (10×3.0 cm, 1:4 EtOAc/petroleum ether) to afford 433 mg (96%) of title compound as a white solid, m.p. 136°-138°.

IR(KBr) 3282, 1625, 1586, 1501, 1452, 1245, 1201, 900, 881, 858, 493, 471 cm$^{-1}$.

270 MHz $^1$H NMR (CDCl$_3$)
5.00 (s, 1H, —OH)
7.10 (m, 2H)
7.41 (d, J=9, 1H)
7.63 (d, J=9, 1H)
7.64 (dd, J=2, 9, 1H)
8.14 (d, J=1, 1H)

MS(CI): 271 (M+H)+.

TLC: Rf (silica gel, 1:4 EtOAc/petroleum ether)=0.32, PMA and UV, homogeneous

The Rf of Part A compound under identical conditions was 0.69.

C. 44-[(6-Iodo-2-naphthalenyl)amino]phenol

A rapidly stirred mixture of 400 mg (1.48 mmol) of Part B compound, 300 mg (2.5 mmol, Aldrich) of 4-aminophenol, 500 mg (4.80 mmol, Aldrich) of sodium bisulfite and 5 ml of $H_2O$ was heated to 160° for 72 hours in a sealed tube. The reaction was cooled, added to 50 ml of $H_2O$ and extracted with two 25 ml portions of ethyl acetate. The combined organic extracts were dried ($MgSO_4$) and concentrated in vacuo to give a solid. The crude solid was purified by flash chromatography (15×3.0 cm, 1:2 EtOAc/petroleum ether) followed by recrystallization (EtOAc/petroleum ether) to afford 425 mg (80%) of title compound as light grey crystals, m.p. 194°-195° (dec.).

IR(KBr) 3409 (broad), 1625, 1583, 1520, 1314, 1250, 868, 116, 475 cm$^{-1}$.

270 MHz $^1$H NMR(CDCl$_3$+DMSO-d$_6$)
6.40 (s, 1H, —NH—)
6.85 (dd, J=2, 6, 2H, benzene aromatics)
7.08 (m, 4H)
7.27 (d, J=9, 1H)
7.51 (d, J=8, 2H)
8.00 (s, 1H)
8.59 (s, 1H, —OH)

67.5 $^{13}$C NMR(CDCl$_3$+DMSO-d$_6$) 85.64, 106.3, 115.8, 119.0, 123.3, 127.4, 129.3, 133.2, 133.3, 134.0, 135.6, 144.3, 153.1

MS(CI): 362 (M+H)+

TLC: Rf (silica gel, 1:2 EtOAc/petroleum ether)=0.35, PMA and UV, homogeneous

The Rf of Part B compound under identical conditions was 0.48.

Anal Calcd for $C_{16}H_{12}INO$: C, 53.21; H, 3.35; N, 3.88 I, 35.13. Found: C, 53.60; H, 3.61; N, 3.75;II, 35.09.

EXAMPLE 14

4-[2-Naphthalenylmethyl)amino]phenol

A solution of 1.00 g (4.5 mmol, Aldrich) of 2-(bromomethyl)naphthalene, 2.46 g (22.6 mmol, 5 eq., Aldrich) of 4-aminophenol and 1.51 g (18.0 mmol, 4 eq.) of sodium bicarbonate in 12 ml of dry HMPA was stirred at 0° C. for 60 minutes. Water was added and this was extracted with EtOAc. The organic layers were combined, dried (MgSO$_4$) and concentrated in vacuo. Purification via flash chromatography (silica gel, 1:5 EtOAc/petroleum ether) afforded 800 mg (71%) of title compound as a white solid: m.p. 120°-121° C.

IR(KBr) 3491, 3327, 1600, 1509, 1421, 1367, 1336, 1307, 1227, 1112, 821, 746 cm$^{-1}$.

270 MHz $^1$H NMR (CDCl$_3$)
5 4.10 (br s, 2H, —NH and OH)
4.43 (s, 2H, H—N—CH$_2$)

6.58 (d, J=9 Hz, 2H, phenol H's)
6.70 (d, J=9 Hz, 2H, phenol H's)
7.43 (m, 3H, aromatic H's)
7.80 (m, 4H, aromatic H's)
MS(CI): 250 (M+H)+

TLC: Rf (silica gel, 1:1 EtOAc/petroleum ether)=0.52, UV and PMA, homogeneous

Anal Calcd for C$_{17}$H$_{15}$NO: C, 81.89; H, 6.07; N, 5.62 Found: C, 81.87; H, 6.10; N, 5.68

EXAMPLE 15

N-(4-Hydroxyphenyl)-N-(6-hydroxy-2-naphthalenyl)acetamide

A solution of 830 mg (3.30 mmol of 6-[(4-hydroxyphenyl)amino]-2-naphthalenol (prepared as described in Example 3) and 840 ul (6.60 mmol, 2 eq.) of dimethylaniline in 15 ml of dry CH$_2$Cl$_2$ and 5 ml of dry THF was stirred at 0° C., then 415 ul (5.80 mmol, Mallinckrodt) of acetyl chloride was added dropwise. After 50 minutes, 1N aqueous HCl was added and this was extracted with EtOAc. The organic layers were washed with 1N aqueous HCl, dried (MgSO$_4$) and concentrated in vacuo. The aqueous layers were extracted with hot EtOAc and the organic layers were combined, dried (MgSO$_4$) and concentrated in vacuo. Purification of all the organic phases was accomplished via flash chromatography (1:2, 1:1 EtOAc/petroleum ether) and recrystallization (aqueous MeOH) afforded 97 mg (10%) of title compound as pale orange crystals: m.p. 255° C.

IR(KBr) 3349, 2799, 2674, 2597, 1606, 1592, 1508, 1472, 1402, 1250, 993, 881, 858, 842 cm$^{-1}$.

270 MHz $^1$H NMR(DMSO-d$_6$)

δ1.93 (s, 3H, COCH$_3$)
6.76 (s, 2H, aromatic H's)
7.10-7.32 (br m, 4H, aromatic H's)
7.67 (s, 4H, aromatic H's)
9.69 (br s, 2H, —NH— and —OH—)
MS(CI): 294 (M+H)+

TLC: Rf (silica gel, 3:1 EtOAc/petroleum ether)=0.38, UV and PMA, homogeneous.

Anal Calcd for C$_{18}$H$_{15}$NO$_3$: C, 73.70; H, 5.15; N, 4.77. Found: C, 73.49; H, 5.22; N, 4.65.

EXAMPLE 16

N-(4-Hydroxyphenyl)-N-(6-methoxy-2-naphthalenyl)acetamide

To a solution of 190 mg (0.72 mmol) of 4-[(6-methoxy-2-naphthyl)amino]phenol (prepared as described in Example 2) and 0.50 ml of pyridine (dried over KOH) in 4 ml of dry CH$_2$Cl$_2$ at 0° was added dropwise over 5 minutes 55 ul (0.77 mmol) of acetyl chloride. The reaction mixture was stirred for 30 minutes then added to 25 ml of 1N aqueous HCl solution and extracted with 25 ml of warm ethyl acetate. The organic extract was washed with an additional 25 ml of 1M aqueous HCl solution, dried (MgSO$_4$) and concentrated in vacuo to give a solid. The crude solid was purified by flash chromatography (silica gel, 10×3.0 cm, 1:1 EtOAc/petroleum ether) followed by recrystallization (EtOAc/petroleum ether) to afford 145 mg (66%) of title compound as white crystals, m.p. 187°-188°.

IR(KBr) 3100 (broad), 1642, 1605, 1511, 1463 1391, 1261, 1241, 1222, 1169, 1031 cm$^{-1}$.

270 MHz $^1$H NMR (DSO-d$_6$)

δ1.94 (s, 3H, acetyl CH$_3$)
3.86 (s. 3H, —OCH$_3$)
6.60-7.95 (m, 10H, aromatic)
9.60 (br s, 1H, —OH)
MS(CI): 308 (M+H)+

TLC: Rf (silica gel, 1:1 EtOAc/petroleum ether==0.21, PMA and UV, homogeneous The Rf of Example 2 compound under identical conditions was 0.60.

Anal Calcd for C$_{19}$H$_{17}$NO$_3$: C, 74.25; H, 5.58; N, 4.56. Found: C, 74.38; H, 5.68; N, 4.56.

EXAMPLE 17

4-[(6-Methoxy-2-naphthyl)methylamino]phenol

A.

2-[(4-Benzyloxyphenyl)amino]-6methoxynaphthalene

The oil was removed from 100 mg (50% in oil, 2.1 mmol, Alfa) of sodium hydride dispersion by washing with three portions of petroleum ether then the residue was covered with 10 ml of dry THF. A total of 530 mg (2.00 mmol) of 4-[(6-methoxy-2-naphthyl)amino]phenol (prepared as described in Example 2) was added to the resulting mixture in several portions. The deep purple reaction mixture was stirred for an additional 10 minutes until hydrogen evolution ceased then 1 ml of sieve-dried DMF was added, followed by 240 ul (2.02 mmol, Aldrich) of benzyl bromide. The solution was heated to 50° for 1 hour, cooled, added to 50 ml of H$_2$O and extracted with 50 ml of ethyl acetate. The organic extract was washed with two additional portions of H$_2$O, dried (MgSO$_4$) and concentrated in vacuo to give 690 mg (97%) of crude title compound as a lavender solid, m.p. 155°-157°.

60 MHz $^1$H NMR(CDCl$_3$)

3.85 (s, 3H, —OCH$_3$)
5.03 (s, 2H, —OCH$_2$Ph)
6.77-7.80 (m, 16H)

TLC: Rf (silica gel), 1:2 EtOAc/petroleum ether)=0.47, PMA and UV, homogeneous The Rf of Example 2 compound under identical conditions was 0.26.

B.

2-[(4-Benzyloxyphenyl)methylamino]-6-methoxynaphthalene

In a stoppered flask a mixture of 675 mg (1.90 mmol) of Part A compound, 235 ul (3.80 mmol, MCB) of iodomethane and 400 mg (4.76 mmol) of powdered sodium bicarbonate in 5 ml of dry HMPA was heated to 50° for 18 hours. The reaction was cooled, added to 25 ml of H$_2$O and extracted with 25 ml of dichloromethane. The organic extract was separated, washed with three 25 ml portions of H$_2$O, dried (Na$_2$SO$_4$) and concentrated in vacuo to give a solid. The crude material was solubilized in dichloromethane and filtered through a pad of neutral alumina((5×3 cm, activity I, CH$_2$Cl$_2$ elution). The filtrate was concentrated in vacuo to afford 598 mg (85%) of title compound as a pale pink solid, m.p. 139°-141°.

60 MHz $^1$H NMR(CDCl$_3$)

3.30 (s, 3H, —NCH$_3$)
3 83 (s, 3H, —OCH$_3$)
5.00 (s, 2H, —OCH$_2$Ph)
6.70-7.70 (m, 15H)
MS(CI): 370 (M+H)+.

TLC: Rf (silica gel, 1:4 EtOAc/petroleum ether)=0.53, PMA and UV, homogeneous The Rf of Part A compound under identical conditions was 0.33.

C. 4-[(6-Methoxy-2-naphthyl)methylamino]phenol

To 40 ml of anhydrous methanol cooled in an ice-bath was added dropwise 0.50 ml (7.0 mmol) of acetyl chloride. The solution was stirred for 15 minutes then under argon, 150 mg of 10% palladium on charcoal catalyst was added in one portion. The mixture was warmed to room temperature then 560 mg (1.52 mmol) of Part B compound was added and the reaction stirred rapidly under an atmosphere of hydrogen (balloon) for 3 hours. The resulting mixture was filtered through a small column (4×2 cm) of sand and the eluant refiltered through a polycarbonate filter. The filtrate was concentrated in vacuo and the residue partitioned between 50 ml of saturated aqueous $NaHCO_3$ solution and 50 ml of ethyl acetate. The organic extract was separated and the aqueous layer extracted with 25 ml of ethyl acetate. The organic extracts were combined in vacuo to give a solid. The crude solid was purified by flash chromatography (10×3.0 cm, 1:4 EtOAc/petroleum ether) followed by recrystallization (EtOAc/petroleum ether) to afford 320 mg (75%) of title compound as pale yellow-green crystals, m.p. 139°–140°.

IR(KBr) 3307, 1605, 1514, 1463, 1391, 1244, 1205, 1166, 1120, 1030, 853, 827 $cm^{-1}$.

270 MHz $^1H$ NMR($CDCl_3$)

3.32 (broadened s, 3H, —$NCH_3$)

3.89 (s, 3H, —$OCH_3$)

4.61 (s, 1H, —OH)

6.80 (d, J=9, 2H, phenol aromatics)

77.05 (m, 6H, aromatics)

7.53 (d, J=10, 1H, aromatic)

7.57 (d, J=9, 1H, aromatic)

MS(CI): 280 $(M+H)^+$

TLC: Rf (silica gel, 1:4 EtOAc/petroleum ether)=0.18, PMA and UV, homogeneous

The Rf of Part B compound identical conditions was 0.51

Anal Calcd for $C_{18}H_{17}NO_2$: C, 77.40; H, 6.13; N, 5.01. Found: C, 77.51; H, 6.14; N, 4.94.

EXAMPLE 18

4-(6-Quinolinylamino)phenol

A. 6-Hydroxyquinoline

A solution of 2.50 g (15.7 mmol, Aldrich) of 6-methoxyquinoline in 10 ml of 48% aqueous HBr was refluxed for 24 hours. The reaction mixture was cooled, added slowly to a 150 ml stirred solution of saturated aqueous sodium bicarbonate and then extracted with two 100 ml portions of ethyl acetate. The organic extracts were combined, dried ($MgSO_4$) and concentrated in vacuo to give a solid. The crude material was recrystallized (EtOAc/petroleum ether) to afford 1.95 g (84%) of title compound as white crystals, m.p. 194°–195°.

IR(KBr) ~3100–2500 (broad), 1637, 1579, 1500, 1417, 1377, 1321, 1268, 1242, 1228, 1159, 1127, 921, 838, 791, 772 $cm^{-1}$.

270 MHz $^1H$ NMR($CDCl_3$+DMSO-$d_6$)

δ7.13 (d, J=3, 1H)

7.31 (dd, J=4, 8, 1H)

7.35 (dd, J=2, 8, 1H)

7.91 (d, J=8, 1H)

7.99 (d, J=7, 1H)

8.67 (dd, J=2,4, 1H)

9.77 (broad s, 1H, —OH)

67.5 MHz $^{13}C$ NMR ($CDCl_3$+DMSO-$d_6$) 107.6, 120.2, 121.3, 128.7, 129.4, 133.4, 142.5, 146.0, 154.8

MS(CI) 148 $(M+H)^+$

TLC: Rf (silica gel, 1:1 EtOAc/petroleum ether)=0.26, UV, homogeneous.

The Rf of 6-methoxyquinoline under identical conditions was 0.39.

B. 4-(6-Quinolinylamino)phenol

A rapidly stirred solution of 300 mg (2.04 mmol) of Part A compound, 272 mg (2.50 mmol, Aldrich) of 4-aminophenol and 500 mg (4.8 mmol, Aldrich) of sodium bisulfite in 5 ml of $H_2O$ was heated to 160° C. in a closed tube for 20 hours. The reaction mixture was cooled, added to 50 ml of $H_2O$ and extracted with two 50 ml portions of hot ethyl acetate. The organic extracts were combined, dried ($MgSO_4$) and concentrated in vacuo to give an orange solid. The crude material was purified by flash chromatography (20×5.0 cm, 1:1:1 EtOAc/$CH_2Cl_2$/petroleum ether) to afford 310 mg (64%) of title compound as a yellow solid, m.p. ~235° C. (dec.).

IR(KBr) 3375, ~3050–2400 (broad), 1624, 1512, 1469, 1383, 1250, 833 $cm^{-1}$.

270 MHz $^1H$ NMR($CDCl_3$+DMSO-$d_6$)

δ6.79 (d, J=8, 2H, phenol aromatics 7.08 (m, 3H)

7.24 (dd, J=4, 8, 1H)

7.37 (dd, J=3, 9, 1H)

7.80 (m, 2H)

7.88 (d, J=8, 1)

8.52 (dd, J=2, 4, 1H)

8.98 (broad s, 1H)

67.5 MHz $^{13}C$ NMR($CDCl_3$+DMSO-$d_6$) 103.0, 114.3, 119.6, 120.6, 121.2, 128.1, 131.9, 141.5, 142.9, 144.2, 151.5

MS(CI): 237 $(M+H)^+$

TLC: Rf (silica gel, 2:1:1 EtOAc/$CH_2Cl_2$/petroleum ether)=0.17, PMA and UV, homogeneous. The Rf of Part A compound and 4-aminophenol under identical conditions was 0.22.

Anal Calcd for $C_{15}H_{12}N_2O$: C, 76.25; H, 5.12; N, 11.86 Found: C, 75.90; H, 5.22;N, 11.81.

EXAMPLES 19 TO 42

Following the procedures as outlined in the Specification and the working Examples, the following additional compounds in accordance with the present invention may be prepared.

| Ex. No. | $R^4$ | $R^1$ (position) | $R^3$ | $(CH_2)_m$ | $R^2$ (position) |
|---|---|---|---|---|---|

Structure:

$$\text{Ar}_1\text{-OR}^4 \text{ with } R^1 \text{ at position 3, and } R^3\text{N-(CH}_2)_m\text{-naphthyl-R}^2$$

(phenyl ring numbered 1-6 with OR⁴ at 1, R¹ at 2/3, R³N- at 4; naphthyl numbered 1-8 with attachment at 2, R² at various positions)

| Ex. No. | $R^4$ | $R^1$ (position) | $R^3$ | $(CH_2)_m$ | $R^2$ (position) |
|---|---|---|---|---|---|
| 19. | H | H | $C_2H_5$ | $CH_2$ | $C_2H_5$ (6) |
| 20. | $CH_3$ | $C_2H_5$ (3) | H | $(CH_2)_2$ | $C_6H_5$ (7) |
| 21. | $CH_3\overset{O}{\underset{\|}{C}}$ | $C_6H_5$ (2) | $C_3H_7\overset{O}{\underset{\|}{C}}$ | $(CH_2)_3$ | OH (6) |
| 22. | H | OH (3) | $C_6H_5\overset{O}{\underset{\|}{C}}$ | $(CH_2)_4$ | $HOCH_2O-$ (7) |
| 23. | $C_2H_5$ | $HO(CH_2)_2O$ (2) | H | $(CH_2)_5$ | $C_2H_5S$ (6) |
| 24. | $C_2H_5\overset{O}{\underset{\|}{C}}$ | $C_2H_5S$ (3) | H | $-CH_2-\underset{CH_3}{CH}-$ | $C_3H_7O$ (8) |
| 25. | H | $CH_3O$ (6) | $C_3H_7$ | $-CH_2-\underset{CH_3}{\overset{CH_3}{C}}-$ | $CH_3CO$ (7) |
| 26. | $C_3H_7$ | H | $C_4H_9\overset{O}{\underset{\|}{C}}$ | $CH_2$ | $C_6H_5\overset{O}{\underset{\|}{C}}O$ (3) |
| 27. | $C_3H_7\overset{O}{\underset{\|}{C}}$ | $C_2H_5CO$ (3) $\overset{O}{\underset{\|}{}}$ | $C_6H_5\overset{O}{\underset{\|}{C}}$ | $(CH_2)_2$ | Cl (4) |
| 28. | H | $C_6H_5CO$ (2) $\overset{O}{\underset{\|}{}}$ | $C_6H_{13}$ | $(CH_2)_3$ | $CO_2H$ (5) |
| 29. | $C_4H_9$ | Cl (5) | $C_5H_{11}$ | $-\underset{CH_3}{CH}-$ | $C_2H_5O\overset{O}{\underset{\|}{C}}$ (6) |
| 30. | $C_4H_9\overset{O}{\underset{\|}{C}}$ | $CO_2H$ (2) | $C_4H_9\overset{O}{\underset{\|}{C}}$ | — | $NH_2\overset{O}{\underset{\|}{C}}$ (6) |
| 31. | H | $CH_3O\overset{O}{\underset{\|}{C}}$ (3) | H | — | $CH_3$ (6) |
| 32. | $C_5H_{11}$ | $NH_2\overset{O}{\underset{\|}{C}}-$ (6) | H | — | $C_2H_5$ (7) |
| 33. | $C_5H_{11}\overset{O}{\underset{\|}{C}}$ | $CH_3\overset{O}{\underset{\|}{C}}NH$ (3) | $CH_3$ | — | H |
| 34. | H | $C_6H_5\overset{O}{\underset{\|}{C}}NH$ (5) | H | — | H |
| 35. | $C_6H_{13}$ | H | $C_2H_5$ | $CH_2$ | $C_3H_7$ (5) |
| 36. | $C_6H_{13}\overset{O}{\underset{\|}{C}}$ | H | H | $(CH_2)_2$ | $C_5H_{11}$ (6) |

-continued

| Ex. No. | R⁴ | R¹ (position) | R³ | (CH₂)ₘ | R² (position) |
|---|---|---|---|---|---|

Structure: OR⁴ on phenyl ring (position 1), R¹ at position 2/3, R³—N—(CH₂)ₘ— linking to naphthyl ring with R² substituent.

| Ex. No. | R⁴ | R¹ (position) | R³ | (CH₂)ₘ | R² (position) |
|---|---|---|---|---|---|
| 37. | H | C₂H₅S (3) | H | CH₂ | Cl (4) |
| 38. | C₂H₅ | CH₃O (6) | C₄H₉ | (CH₂)₃ | CO₂H (5) |
| 39. | C₃H₇C(=O) | H | C₅H₁₁C(=O) | — | C₂H₅C(=O) (3) |
| 40. | H | C₆H₅CO (2) | H | —CH₂—CH(CH₃)— | C₃H₇OC(=O) (5) |
| 41. | C₇H₁₅ | Cl (6) | CH₃ | (CH₂)₆ | NH₂C(=O) (2) |
| 42. | C₃H₇ | CO₂H (5) | C₆H₅C(=O) | (CH₂)₄ | CH₃O (7) |

EXAMPLE 43

A formulation suitable for oral administration in the treatment of bronchoconstriction or asthma is set out below.

1000 tablets each containing 100 mg of 4-[(6-methoxy-2-naphthyl)amino]phenol (prepared in Example 2) are produced from the following ingredients:

| | |
|---|---|
| 4-[(6-Methoxy-2-naphthyl)amino]phenol | 100 g |
| Corn starch | 50 g |
| Gelatin | 7.5 g |
| Avicel (microcrystalline cellulose) | 25 g |
| Magnesium stearate | 2.5 g |

The 4-[(6-methoxy-2-naphthyl)amino]phenol and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 200 mg of active ingredients which is used for treating bronchoconstriction or asthma.

EXAMPLE 44

By substituting 100 g of 4-[(6-methoxy-2-naphthyl)methylamino]phenol (prepared in Example 17) for 4-[(6-methoxy-2-naphthyl)amino]phenol in Example 1, 1000 tablets each containing the 4-[(6-methoxy-2-naphthyl)methylamino]phenol are produced which is useful in treating asthma.

EXAMPLE 45

Two piece #1 gelatin capsules each containing 250 mg of 4-[(6-pentyl-2-naphthalenyl)amino]phenol are filled with a mixture of the following ingredients:

| | |
|---|---|
| 4-[(6-Pentyl-2-naphthalenyl)amino]phenol | 250 mg |
| Magnesium stearate | 7 mg |
| USP lactose | 193 mg |

The resulting capsules are useful in treating psoriasis or inflammation.

EXAMPLE 46

Tablets for use in treating asthma are prepared following the procedure of Example 43 except that 4-[(2-naphthalenylamino)phenol (prepared as in Example 1) is employed in place of 4-[(6-methoxy-2-naphthyl)amino]phenol.

EXAMPLE 47

Tablets for use in treating psoriasis are prepared following the procedure of Example 43 except that 6-[(4-hydroxyphenyl)amino]-2-naphthalenol (prepared as in Example 3) is employed in place of 4-[(6-methoxy-2-naphthyl)amino]phenol.

EXAMPLE 48

Tablets for use in treating inflammation are prepared following the procedure of Example 43 except that 4-[[6-(methylthio)-2-naphthalenyl]amino]phenol (prepared as in Example 5) is employed in place of 4-[(6-methoxy-2-naphthyl)amino]phenol.

EXAMPLE 49

Tablets for use in treating hypertension are prepared following the procedure of Example 43 except that 6-[(4-hydroxyphenyl)amino]naphthalene2-amide (prepared as in Example 8) is employed in place of 4-[(6-methoxy-2-naphthyl)amino]phenol.

It will be appreciated that all of the compounds as prepared in Examples 1 to 42 may be formulated in oral dosage forms as described above.

EXAMPLE 50

The above Example 2 compound, namely, 4-[(6-methoxy-2-naphthyl)amino]phenol

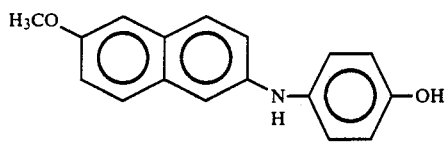

and Example 17 compound, namely, 4[(6-methoxy-2naphthyl)methylamino]phenol

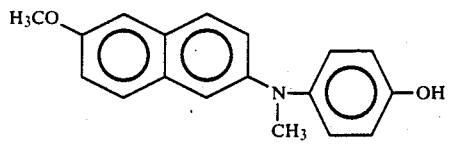

were tested against the Example 1 compound of U.S. Pat. No. 4,496,590 to Schlegel et al, that is, 2-5-methoxybenzenemethanol

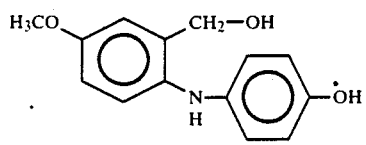

for oral activity in a standard assay for inhibitors of SRS-mediated bronchoconstriction in sensitized guinea pigs. A compound having activity in the above assay would be considered as having antiasthmatic activity.

The test employed was similar to that employed in U.S. Pat. No. 4,496,590 to Schlegel et al except that in the present test the test compounds were administered perorally while in the Schlegel et al procedure, the compounds were administered intravenously.

The following test procedure was employed.

Standard Assay for Inhibitors of SRS-Mediated Bronchoconstriction in Sensitized Guinea Pigs Guinea pigs sensitized to ovalbumin and challenged intravenously with this antigen in the presence of the cyclooxygenase inhibitor, indomethacin (IM), an antihistamine, methapyriline, and a beta-antagonist, propranolol, undergo a delayed (3-13 minutes) bronchospasm, presumed due to the synthesis and release of SRS (leukotriene C, D, and E). A Buxco respiratory mechanics analyzer is used to evaluate the in vivo efficacy of inhibitors of the lipoxygenase pathway in this model of SRS-mediated bronchoconstriction. This system monitors pulmonary air flow, through use of a whole body plethysomgraph, and transpulmonary pressure, from tracheal and intrapleural catheters. Tidal volume is derived from the flow signal by integration, and airway resistance (R) and dynamic compliance ($C_{dyn}$) are continuously computed by the system from the primary flow, volume, and pressure parameters. In addition, the system continuously monitors blood pressure and heart rate.

The method used to sensitize animals and induce bronchoconstriction are modifications of those described by Ritchie, et al. [Ritchie, D. M., et al, Agents and Actions 11:396, (1981)]. Male Hartly guinea pigs (200 g) ar sensitized by injecting ovalbumin (OA) (10 mg/kg) (each injection also contains 16 mg Amphojel) ip o days 0 and 2. These animals are normally used on days 10-18 following initial sensitization.

On the test day animals are anesthetized by ip injection of urethane (1.2-1.5 g/kg. The jugular vein and carotid artery are catheterized using intramedic PR50 tubing. The trachea is catheterized using intramedic PE240 tubing. Spontaneous respiration is arrested by injecting succinyl choline (2.0 mg/kg, iv) into the jugular vein, and the animal is artificially respirated at 48 breaths/minute with a volume of 4.0 ml/breath. Intramedic PE200 tubing is inserted through the chest wall into the intrapleural space, and the tracheal (by sidearm attachment) and intrapleural cannulas are attached to a single pressure transducer in order to obtain the transpulmonary pressure. The standard protocol requires an initial injection of indomethacin (meglumine salt) (10 mg/kg, iv). Five minutes later antihistamine (methapyrilene, 2 mg/kg, iv) is given, followed one minute later by propranolol (0.1 mg/kg, iv) to induce leukotriene induced bronchoconstriction with no histamine-induced bronchoconstriction and no beta-agonistic bronchoconstriction. Respiratory parameters are then allowed to stabilize for 5-15 minutes. Drugs are tested for oral activity by giving the compound by gavage to 18 hour fasted animals one hour prior to anesthetization. At restabilization, base lines are recorded by the computer for all parameters. To induce bronchoconstriction, a challenge dose of OA (0.4 mg/kg, iv) is given. Under these standard conditions a delayed (3-13 minutes) bronchoconstriction is observed which is long lasting (>15 minutes). This bronchoconstriction is characterized by a significant drop in $C_{dyn}$ and a 200-400% increase in R. The challenge dose of 0.4 mg/kg OA generally produces an intermediate to sever bronchospasm resulting in an average 80% drop in $C_{dyn}$ and a 200-400% increase in R. This SRS-mediated bronchoconstriction differs significantly from that produced by histamine, which is very rapid in onsert (5-15 seconds), and which is transient (peak response lasting 1-3 minutes).

The SRS-antagonist FPL-55712 was tested as a standard in this model, and given iv less than one minute before OA challenge. It inhibited (100% inhibition at 10 mg/kg) the bronchoconstriction as measured by effects on R and $C_{dyn}$.

$$C_{dyn}$$
$$(ED_{50}^{R} = 0.11 \text{ mg/kg}, ED_{50} = 1.0 \text{ mg/kg})$$

Results:

Results are expressed as % of baseline values after antigen challenge for R and $C_{dyn}$, and percent inhibition is calculated by comparing % changes in baseline values between control (vehicle) and drug treated test groups. The effective dose producing 50% inhibition ($ED_{50}$) will be determined where possible for both $C_{dyn}$ and R ($ED_{50}\,^{50}dyn$, $ED_{50}^{R}$).

Statistical significance is determined using a two tailed, unpaired T-test. Drug effects with $p < 0.05$ will be considered significant.

Test compounds were evaluated for their ability to inhibit SRS-mediated changes in dynamic compliance ($C_{dyn}$) and resistance (R) as compared to the medicated (indomethacin-methapyrilenepropranolol) control group.

The results obtained are set out in the following Table which shows that the Schlegel et al Example 1 compound (referred to as SQ 30,624) was orally inactive at a dose of 50 mg/kg while the Example 2 compound of the invention (referred to as SQ330,645) was orally active, displaying ED$_{50}$ values of 23.8mg/kg and 6 mg/kg for inhibition of SRS-mediated changes in dynamic compliance and resistance, respectively. The Example 17 compound (referred to as SQ 30,988) also significantly inhibited antigen-induced bronchoconstriction.

In view of the above data, it is seen that the compounds of Examples 2 and 17 exhibit antiasthmatic activity when administered orally while the test compound of Schlegel et al did not have antiasthmatic activity when administered orally.

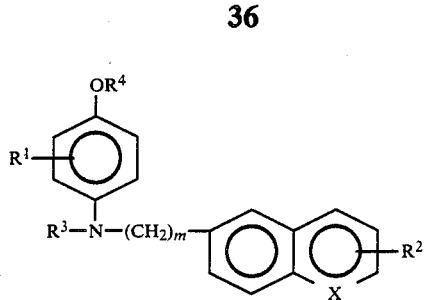

wherein m is 0 to 5; X is CH or N; $R^1$ and $R^2$ may be the same or different and are H, lower alkyl, aryl, hydroxy, hydroxyalkyleneoxy, alkylthio, alkoxy, alkanoyloxy, aroyloxy, halo, carboxy, alkoxycarbonyl or amido; $R^3$ is H, lower alkyl, alkanoyl or aroyl; and $R^4$ is H, lower alkyl, alkanoyl or benzoyl, and including acid-addition salts thereof, with the proviso that when $R^4$ is benzoyl.

TABLE

| | Dynamic Compliance ($C_{dyn}$) [% of Baseline following Antigen Challenge] (Mean ± S.E.) | Inhibition (%) | Resistance (R) [% of Baseline following Antigen Challenge] (Means ± S.E. | Inhibition (%) |
|---|---|---|---|---|
| | Compound Tested 4-[(6-Methoxy-2-naphthyl) amino]phenol (Example 2) SQ 30,645 | | | |
| Control Vehicle (n = 19) 0.1% Tween 80/H$_2$O | 21 ± 1 | — | 407 ± 16 | |
| Drug Dose (mg/kg) | | | | |
| 5.0 (n = 4) | 23 ± 7 | 3 | 335 ± 74 | 23 |
| 12.5 (n = 6) | 44 ± 5 | 33 | 231 ± 39 | 57 |
| 25.0 (n = 5) | 62 ± 7 | 52 | 194 ± 42 | 69 |
| 50.0 (n = 5) | 66 ± 4 | 57 | 149 ± 11 | 84 |
| | ED$_{50}^{Cdyn}$ = 23.8(14.1–51.7)mg/kg | | ED$_{50}^{R}$ = 6.0(1.3–2.7mg/kg | |

Route of Antigen Challenge: i.v.
Route of Drug Administration: P.O.
Vehicle: 0.1% Tween 80/H$_2$O
Time Interval Between Drug and Antigen Challenge: One Hour
Comments: SQ 30,645 was administered as a fine homogeneous suspension, one hour prior to antigen challenge of 18 hour fasted guinea pigs. SQ 30,645 was orally active, displaying compliance and resistance, respectively.

| | Compound Tested 4-[(6-Methoxy-2-naphthyl) methylamino]phenol (Example 17) SQ 30,988 | | | |
|---|---|---|---|---|
| Control Vehicle (N = 23) | 19 ± 4 | — | 377 ± 50 | |
| Drug Dose (mg/kg) | | | | |
| 25.0 (N = 6) | 57 ± 10 | 47 | 149 ± 23 | 82 |
| 12.5 (N = 9) | 64 ± 7 | 56 | 136 ± 10 | 88 |
| 9.0 (N = 6) | 64 ± 8 | 56 | 141 ± 28 | 85 |
| 6.0 (N = 4) | 31 ± 20 | 15 | 374 ± 132 | 1 |
| 3.0 (N = 5) | 19 ± 11 | 0 | 467 ± 134 | 0 |
| | 9.0 mg/kg > ED$_{50}^{Cdyn}$ > 6.0 mg/kg | | 9.0 mg/kg > ED$_{50}^{R}$ > 6.0 mg/kg | |

Route of Antigen Challenge: i.v.
Route of Drug Administration: P.O.
Vehicle: H$_2$O/Tween 80, 0.1%
Time Interval Between Drug and Antigen Challenge: One Hour
Coments: SQ 30,988 significantly inhibited antigen-induced bronchoconstriction given PO one hour before antigen challenge.

| | Compound Tested 2-[(4-Hydroxyphenyl) amino]-5-methoxybenzenemethanol (Example 1 of Schlegel U. S. Pat. No. 4,496,590) | | | |
|---|---|---|---|---|
| Control Vehicle (N = 20) 0.1% Tween 80/H$_2$O | 13 ± 1 | — | 439 ± 15 | — |
| Drug Dose (mg/kg) | | | | |
| 50.0 (n = 3) | 4 ± 3 | 0 | 386 ± 64 | 15 |
| | ED$_{50}^{Cdyn}$ = | | ED$_{50}^{R}$ | |

Route of Antigen Challenge: i.v.
Route of Drug Administration: P.O.
Vehicle: 0.1% Tween 80/H$_2$O
Time Interval Between Drug and Antigen Challenge: One Hour
Comments: Test compound was orally inactive at a dose of 50 mg/kg.

What is claimed is:

1. A method of inhibiting leukotriene biosynthesis to treat inflammation or psoriasis, or for treating asthma, which comprises orally administering to a mammalian host in need of such treatment an effective amount of a compound of the structure $R^2$ is other than H; or a compound of the structure

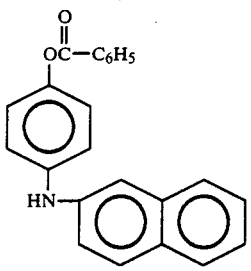

or a pharmaceutically acceptable salt thereof.

2. The method as defined in claim 1 where in the compound employed R⁴ is H.

3. The method as defined in claim 2 where in the compound employed R¹ is H.

4. The method as defined in claim 1 where in the compound employed R³ is H and m is 0.

5. The method as defined in claim 1 where in the compound employed X is CH.

6. The method as defined in claim 1 where in the compound employed X is N.

7. The method as defined in claim 1 where the compound employed has the name 4-[(6-bromo or 6-iodo-2-naphthalenyl]amino]phenol.

8. The method as defined in claim 1 where the compound employed has the name 4-[(6-pentyl-2-naphthalenyl)amino]phenol.

9. The method as defined in claim 1 where the compound employed has the name 6-[(4-hydroxyphenyl)amino]-2-naphthalene carboxylic acid or its methyl ester.

10. The method as defined in claim 1 where the compound employed has the name 4-[[6-amido-2-naphthalenyl]amino]phenol.

11. The method as defined in claim 1 where the compound employed has the name 4-[[6-(methylthio)-2-naphthalenyl]amino]phenol.

12. The method as defined in claim 1 where the compound employed has the name 4-[(6-butoxy-2-naphthalenyl)amino]phenol.

13. The method as defined in claim 1 where the compound employed has the name 4-[[6-[(4-hydroxyphenyl)amino]-2-naphthalenyl]oxy]butanol.

14. The method as defined in claim 1 where the compound employed has the name N-(4-hydroxyphenyl)-N-(6-methoxy- or 6-hydroxy-2-naphthalenyl)acetamide.

15. The method as defined in claim 1 where the compound employed has the name 4-[(6-methoxy--naphthyl)methylamino]phenol.

16. The method as defined in claim 1 where the compound employed has the name 4-[(2-naphthalenylmethyl)amino]phenol.

17. The method as defined in claim 1 where the compound employed has the name 4-(6-quinolinylamino)phenol.

18. The method as defined in claim 1 where the compound employed is 4-[(6-methoxy-2-naphthyl)amino]phenol.

19. The method as defined in claim 1 wherein said compound is administered in an amount within the range of from about 1 to about 100 mg/kg.

20. A method for treating asthma in a mammalian species in need of such treatment, which comprises orally administering to a mammalian host an effective amount of a compound having the structure

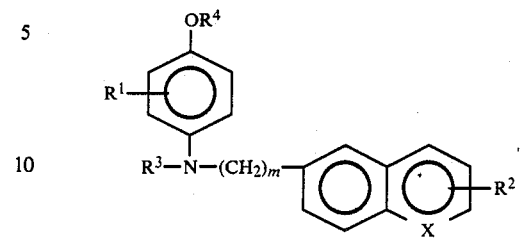

wherein m is 0 to 5; X is CH or N; R¹ and R² may be the same or different and are H, lower alkyl, aryl, hydroxy, hydroxyalkyleneoxy, alkylthio, alkoxy, alkanoloxy, aryloxy, halo, carboxy, alkoxycarbonyl or amido; R³ is H, lower alkyl, alkanoyl or aroyl, and R⁴ is H, lower alkyl, alkanoyl or benzoyl, and including acid-addition salts thereof, with the proviso that when R⁴ is benzoyl, R² is other than H; or a compound of the structure

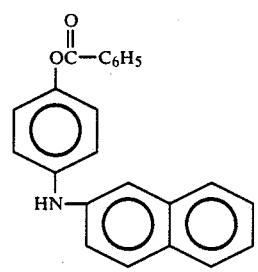

or a pharmaceutically acceptable sat thereof.

21. The method as defined in claim 1 wherein the compound administered has the formula

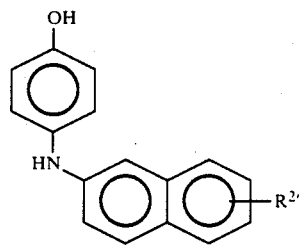

wherein R²', is alkoxy, H or OH.

22. The method as defined in claim 20 wherein the compound administered has the formula

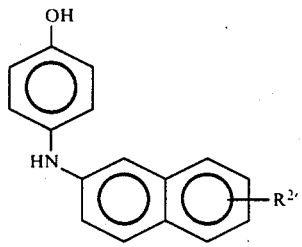

wherein R²', is alkoxy, H or OH.

* * * * *